(12) United States Patent
Xi et al.

(10) Patent No.: US 9,029,520 B2
(45) Date of Patent: May 12, 2015

(54) B7-1-PE40KDEL EXOTOXIN FUSION GENE-BASED DNA VACCINE AND THE USE THEREOF

(75) Inventors: Yongzhi Xi, Beijing (CN); Yuan Luo, Beijing (CN)

(73) Assignee: Affiliated Hospital of Academy of Military Medical Sciences, PLA, Beijing (CN)

(*) Notice: Subject to any disclaimer, the term of this patent is extended or adjusted under 35 U.S.C. 154(b) by 0 days.

(21) Appl. No.: 13/993,685

(22) PCT Filed: Sep. 20, 2011

(86) PCT No.: PCT/CN2011/079862
§ 371 (c)(1),
(2), (4) Date: Jun. 13, 2013

(87) PCT Pub. No.: WO2012/094905
PCT Pub. Date: Jul. 19, 2012

(65) Prior Publication Data
US 2013/0344101 A1 Dec. 26, 2013

(30) Foreign Application Priority Data
Jan. 14, 2011 (CN) .......................... 2011 1 0023985

(51) Int. Cl.
| | | |
|---|---|---|
| C07H 21/02 | (2006.01) |
| C12N 15/00 | (2006.01) |
| C07K 1/00 | (2006.01) |
| A61K 48/00 | (2006.01) |
| C07K 14/00 | (2006.01) |
| C07K 14/21 | (2006.01) |
| C07K 14/705 | (2006.01) |
| A61K 39/00 | (2006.01) |

(52) U.S. Cl.
CPC ............... *C07K 14/001* (2013.01); *C07K 14/21* (2013.01); *C07K 14/70532* (2013.01); *A61K 39/001* (2013.01); *A61K 2039/53* (2013.01); *C07K 2319/04* (2013.01); *C07K 2319/55* (2013.01)

(58) Field of Classification Search
CPC .................................................. C07K 14/001
See application file for complete search history.

(56) References Cited

U.S. PATENT DOCUMENTS

| 5,980,895 | A | 11/1999 | Pastan et al. |
| 6,074,644 | A | 6/2000 | Pastan et al. |
| 6,492,498 | B1 | 12/2002 | Vallera et al. |
| 7,829,064 | B2 | 11/2010 | Griffiths et al. |
| 7,892,827 | B2 | 2/2011 | Matschiner et al. |
| 2004/0219203 | A1 | 11/2004 | Griffiths et al. |
| 2009/0042785 | A1 | 2/2009 | Matschiner et al. |
| 2011/0123480 | A1 | 5/2011 | Wallach |

FOREIGN PATENT DOCUMENTS

| CN | 1498902 | * | 5/2004 |
| CN | 101343328 | A | 1/2009 |
| CN | 101824424 | A | 9/2010 |
| CN | 1012161998 | A | 6/2011 |
| WO | WO 97/13529 | A1 | 4/1997 |
| WO | WO 03/051926 | A2 | 6/2003 |
| WO | WO 2004/110390 | A2 | 12/2004 |
| WO | WO 2006/001023 | A2 | 1/2006 |
| WO | WO 2006/037960 | A2 | 4/2006 |
| WO | WO 2006/056464 | A2 | 6/2006 |

OTHER PUBLICATIONS

International Search Report issued Dec. 29, 2011 in PCT/CN2011/079862.
Huill Zhang, et al., The Prediction of the Molecular Biology Characteristic of Recombinant Fusion Exotoxin B7-1-Linker-PE40 and B7-2-Linker-PE40, Journal of Experimental Hematology, ISSN: 1009-2137, vol. 9, No. 4, Dec. 31, 2001, pp. 327-332.
Xiaomei Hu, et al., Research advances in Pseudomones aeruginosa exotoxin A gene expression, Progress in Microbiology and Immunology, ISSN: 1005-5673, vol. 32, No. 3, Dec. 31, 2004, pp. 73-75.
Chao-Wei Liao, et al., "Fusion Protein Vaccine by Domains of Bacterial Exotoxin Linked with a Tumor Antigen Generates Potent Immunologic Responses and Antitumor Effects", Cancer Research, vol. 65, No. 19, Oct. 1, 2005, pp. 9089-9098.
Bharal M. Joshi, et al. "Optimization of expression and purification of two biologically active chimeric fusion proteins that consist of human interleukin-13 and *Pseudomonas* exotoxin in *Escherichia coli*", Proteins Expression and Purification, vol. 39, No. 2. Feb. 28, 2005, pp. 189-198.
Extended European Search Report issued Apr. 8, 2014, in European Patent Application No. 11855878.2.

* cited by examiner

*Primary Examiner* — Albert Navarro
(74) *Attorney, Agent, or Firm* — Oblon, McClelland, Maier & Neustadt, L.L.P.

(57) ABSTRACT

The present invention relates to the fields of immunology and molecular biology and related to a B7-1-PE40KDEL exotoxin fusion gene-based DNA vaccine and the use thereof. Specifically, the DNA vaccine contains a recombinant expression vector, and the vector contains exotoxin fusion gene B7-1-PE40KDEL, which is effectively ligated into selected eukaryotic expression vectors, such as pcDNA3.1/Zeo(+), pWLNEO, pSV2CAT, pOG44, pXT1, pSG, pSVK3, pBPV, pMSG, pSVL, and adenovirus. The invention also relates to the exotoxin fusion gene B7-1-PE40KDEL, the encoded exotoxin fusion protein, a recombinant expression vector that contains the exotoxin fusion gene, and compositions that contain the recombinant expression vector. The DNA vaccine in this invention has a good effect on the treatment or prevention of allogeneic tissue/organ transplant rejection and hematopoietic stem cell transplantation rejection such as GVHD.

19 Claims, 20 Drawing Sheets

Figure 1:
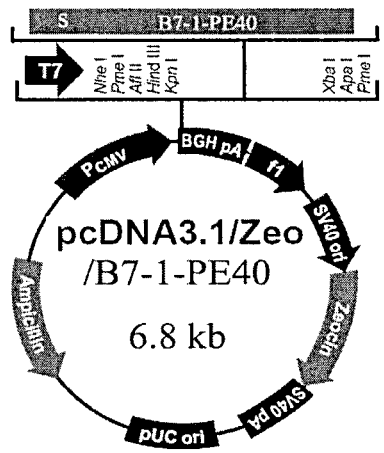

Lane 1: DNA marker
Lane 2: B7-1-PE40KDEL
Lane 3: B7-2-PE40KEDL
Lane 4: B7-1-PE40KDEL +B7-2-PE40KEDL
Lane 5: Naked vector pcDNA3.1
Lane 6: CsA+MTX
Lane 7: Untreated

SEQUENCE LISTING

```
<160> NUMBER OF SEQ ID NOS: 13

<210> SEQ ID NO 1
<211> LENGTH: 1850
<212> TYPE: DNA
<213> ORGANISM: Artificial Sequence
<220> FEATURE:
<223> OTHER INFORMATION: Nucleotide sequence of B7-1-PE40KDEL exotoxin
      fusion gene

<400> SEQUENCE: 1
cgtttaactt aagcttggta cctatggaga cagacacact cctgctatgg gtactgctgc      60
tctgggttcc aggttccact ggtgacgtta tccacgtgac caaggaagtg aaagaagtag     120
caacgctgtc ctgtggtcac aatgtttctg ttgaagagcc ggcacaaact cgcatctact     180
ggcaaaagga gaagaaaatg gtgctgacta tgatgtctgg ggacatgaat atatggcccg     240
```

| | | | | | |
|---|---|---|---|---|---|
| agtacaagaa | ccggaccatc | tttgatatta | ctaataacct | ctccattgtg | atcctggctc | 300 |
| tgcgcccatc | tgacgagggc | acatacgagt | gtgttgttct | gaagtatgaa | aaagacgctt | 360 |
| tcaagcggga | acacctggct | gaagtgacgt | tatcagtcaa | agctgacttc | cctacaccta | 420 |
| gtatatctga | ctttgaaatt | ccaacttcta | atattagaag | gataatttgc | tcaacctctg | 480 |
| gaggttttcc | agagcctcac | ctctcctggt | tggaaaatgg | agaagaatta | agtgccatca | 540 |
| acacaacagt | ttcccaagat | cctgaaactg | agctctatgc | tgttagcagc | aaactggatt | 600 |
| tcaatatgac | aaccaaccac | agcttcatgt | gtctcatcaa | gtatggacat | ttaagagtga | 660 |
| atcagacctt | caactggaat | acaaccaagc | aagagcattt | tcctgataac | ggtggcggcg | 720 |
| gatctggagg | cggtggaagc | ggtggtggct | cgggcggtgg | tgggtcgggc | ggcagcctgg | 780 |
| ccgcgctgac | cgcgcaccag | gcttgccacc | tgccgctgga | gacttccacc | cgtcatcgcc | 840 |
| agccgcgcgg | ctgggaacaa | ctggagcagt | gcggctatcc | ggtgcagcgg | ctggtcgccc | 900 |
| tctacctggc | ggcgcggctg | tcgtggaacc | aggtcgacca | ggtgatccgc | aacgccctgg | 960 |
| ccagccccgg | cagcggcggc | gacctgggcg | aagcgatccg | cgagcagccg | gagcaggccc | 1020 |
| gtcttgccct | gaccctggcc | gccgccgaga | gcgagcgctt | cgtccggcag | ggcaccggca | 1080 |
| acgacgaggc | cggcgcggcc | aacgccgacg | tggtgagcct | gacctgcccg | gtcgccgccg | 1140 |
| gtgaatgcgc | gggcccggcg | gacagcggcg | acgccctgct | ggagcgcaac | tatcccactg | 1200 |
| gcgcggagtt | cctcggcgac | ggcggcgacg | tcagcttcag | caccccgcgg | acgcagaact | 1260 |
| ggacggtgga | gcggctgctc | caggcgcacc | gccaactgga | ggagcgcggc | tatgtgttcg | 1320 |
| tcggctacca | cggcaccttc | ctcgaagcgt | cgcaaagcat | cgtcttcggc | ggggtgcgcg | 1380 |
| cgcgcaacca | ggacctcgac | gcgatctggc | gcggtttcta | tatcgccggc | gatccggcgc | 1440 |
| tggcctacgc | ctacgcccag | gaccaggaac | ccgacgcacg | cggccggatc | cgcaacggtg | 1500 |
| ccctgctgcg | ggtctatgtg | ccgcgctcga | gcctgccggg | cttctaccgc | accagcctga | 1560 |
| ccctggccgc | gccggaggcg | gcgggcgagg | tcgaacggct | gatcggccat | ccgctgccgc | 1620 |
| tgcgcctgga | cgccatcacc | ggccccgagg | aggaaggcgg | gcgcctggag | accattctcg | 1680 |
| gctgccgct | ggccgagcgc | accgtggtga | ttccctcggc | gatccccacc | gacccgcgca | 1740 |
| acatcggcgg | cgacctcgac | ccgtccagca | tccccgacaa | ggaacaggcg | atcagcgccc | 1800 |
| tgccggacta | cgccagccag | cccggcaaac | cgccgaagga | cgagctgtaa | | 1850 |

<210> SEQ ID NO 2
<211> LENGTH: 1827
<212> TYPE: DNA
<213> ORGANISM: Artificial Sequence
<220> FEATURE:
<223> OTHER INFORMATION: Open reading frame of nucleotide sequence of
      B7-1-PE40KDEL exotoxin fusion gene

<400> SEQUENCE: 2
atggagacag acacactcct gctatgggta ctgctgctct gggttccagg ttccactggt 60
gacgttatcc acgtgaccaa ggaagtgaaa gaagtagcaa cgctgtcctg tggtcacaat 120
gtttctgttg aagagccggc acaaactcgc atctactggc aaaaggagaa gaaaatggtg 180
ctgactatga tgtctgggga catgaatata tggcccgagt acaagaaccg gaccatcttt 240
gatattacta ataacctctc cattgtgatc ctggctctgc gcccatctga cgagggcaca 300
tacgagtgtg ttgttctgaa gtatgaaaaa gacgctttca agcgggaaca cctggctgaa 360
gtgacgttat cagtcaaagc tgacttccct acacctagta tatctgactt tgaaattcca 420

-continued

```
acttctaata ttagaaggat aatttgctca acctctggag gttttccaga gcctcacctc    480
tcctggttgg aaaatggaga agaattaagt gccatcaaca caacagtttc caagatcct     540
gaaactgagc tctatgctgt tagcagcaaa ctggatttca atatgacaac caaccacagc    600
ttcatgtgtc tcatcaagta tggacattta agagtgaatc agaccttcaa ctggaataca    660
accaagcaag agcattttcc tgataacggt ggcggcggat ctggaggcgg tggaagcggt    720
ggtggctcgg gcggtggtgg gtcgggcggc agcctggccg cgctgaccgc gcaccaggct    780
tgccacctgc cgctggagac ttccacccgt catcgccagc gcgcggctg ggaacaactg     840
gagcagtgcg gctatccggt gcagcggctg gtcgccctct acctggcggc gcggctgtcg    900
tggaaccagg tcgaccaggt gatccgcaac gccctggcca gccccggcag cggcggcgac    960
ctgggcgaag cgatccgcga gcagccggag caggccgtc ttgccctgac cctggccgcc    1020
gccgagagcg agcgcttcgt ccggcagggc accgcaacg acgaggccgg cgcggccaac    1080
gccgacgtgg tgagcctgac ctgcccggtc gccgccggtg aatgcgcggg ccggcggac    1140
agcggcgacg ccctgctgga gcgcaactat cccactggcg cggagttcct cggcgacggc    1200
ggcgacgtca gcttcagcac ccgcggcacg cagaactgga cggtggagcg gctgctccag    1260
gcgcaccgcc aactggagga gcgcggctat gtgttcgtcg gctaccacgg caccttcctc    1320
gaagcgtcgc aaagcatcgt cttcggcggg gtgcgcgcgc gcaaccagga cctcgacgcg    1380
atctggcgcg gtttctatat cgccggcgat ccggcgctgg cctacggcta cgcccaggac    1440
caggaacccg acgcacgcgg ccggatccgc aacggtgccc tgctgcgggt ctatgtgccg    1500
cgctcgagcc tgccgggctt ctaccgcacc agcctgaccc tggccgcgcc ggaggcggcg    1560
ggcgaggtcg aacggctgat cggccatccg ctgccgctgc gcctggacgc catcaccggc    1620
cccgaggagg aaggcgggcg cctggagacc attctcggct ggccgctggc cgagcgcacc    1680
gtggtgattc cctcggcgat ccccaccgac ccgcgcaaca tcggcggcga cctcgacccg    1740
tccagcatcc ccgacaagga acaggcgatc agcgccctgc cggactacgc cagccagccc    1800
ggcaaaccgc cgaaggacga gctgtaa                                       1827
```

<210> SEQ ID NO 3
<211> LENGTH: 608
<212> TYPE: PRT
<213> ORGANISM: Artificial Sequence
<220> FEATURE:
<223> OTHER INFORMATION: Peptide sequence encoded by B7-1-PE40KDEL
    exotoxin fusion gene

<400> SEQUENCE: 3

Met Glu Thr Asp Thr Leu Leu Leu Trp Val Leu Leu Leu Trp Val Pro
1               5                   10                  15

Gly Ser Thr Gly Asp Val Ile His Val Thr Lys Glu Val Lys Glu Val
                20                  25                  30

Ala Thr Leu Ser Cys Gly His Asn Val Ser Val Glu Glu Pro Ala Gln
            35                  40                  45

Thr Arg Ile Tyr Trp Gln Lys Glu Lys Lys Met Val Leu Thr Met Met
        50                  55                  60

Ser Gly Asp Met Asn Ile Trp Pro Glu Tyr Lys Asn Arg Thr Ile Phe
65                  70                  75                  80

Asp Ile Thr Asn Asn Leu Ser Ile Val Ile Leu Ala Leu Arg Pro Ser
                85                  90                  95

Asp Glu Gly Thr Tyr Glu Cys Val Val Leu Lys Tyr Glu Lys Asp Ala
            100                 105                 110

-continued

```
Phe Lys Arg Glu His Leu Ala Glu Val Thr Leu Ser Val Lys Ala Asp
        115                 120                 125
Phe Pro Thr Pro Ser Ile Ser Asp Phe Glu Ile Pro Thr Ser Asn Ile
    130                 135                 140
Arg Arg Ile Ile Cys Ser Thr Ser Gly Gly Phe Pro Glu Pro His Leu
145                 150                 155                 160
Ser Trp Leu Glu Asn Gly Glu Glu Leu Ser Ala Ile Asn Thr Thr Val
                165                 170                 175
Ser Gln Asp Pro Glu Thr Glu Leu Tyr Ala Val Ser Ser Lys Leu Asp
            180                 185                 190
Phe Asn Met Thr Thr Asn His Ser Phe Met Cys Leu Ile Lys Tyr Gly
        195                 200                 205
His Leu Arg Val Asn Gln Thr Phe Asn Trp Asn Thr Thr Lys Gln Glu
    210                 215                 220
His Phe Pro Asp Asn Gly Gly Gly Ser Gly Gly Gly Ser Gly
225                 230                 235                 240
Gly Gly Ser Gly Gly Gly Ser Gly Gly Ser Leu Ala Ala Leu Thr
                245                 250                 255
Ala His Gln Ala Cys His Leu Pro Leu Glu Thr Ser Thr Arg His Arg
        260                 265                 270
Gln Pro Arg Gly Trp Glu Gln Leu Glu Gln Cys Gly Tyr Pro Val Gln
    275                 280                 285
Arg Leu Val Ala Leu Tyr Leu Ala Ala Arg Leu Ser Trp Asn Gln Val
    290                 295                 300
Asp Gln Val Ile Arg Asn Ala Leu Ala Ser Pro Gly Ser Gly Gly Asp
305                 310                 315                 320
Leu Gly Glu Ala Ile Arg Glu Gln Pro Glu Gln Ala Arg Leu Ala Leu
                325                 330                 335
Thr Leu Ala Ala Ala Glu Ser Glu Arg Phe Val Arg Gln Gly Thr Gly
            340                 345                 350
Asn Asp Glu Ala Gly Ala Ala Asn Ala Asp Val Val Ser Leu Thr Cys
        355                 360                 365
Pro Val Ala Ala Gly Glu Cys Ala Gly Pro Ala Asp Ser Gly Asp Ala
    370                 375                 380
Leu Leu Glu Arg Asn Tyr Pro Thr Gly Ala Glu Phe Leu Gly Asp Gly
385                 390                 395                 400
Gly Asp Val Ser Phe Ser Thr Arg Gly Thr Gln Asn Trp Thr Val Glu
                405                 410                 415
Arg Leu Leu Gln Ala His Arg Gln Leu Glu Glu Arg Gly Tyr Val Phe
            420                 425                 430
Val Gly Tyr His Gly Thr Phe Leu Glu Ala Ala Gln Ser Ile Val Phe
        435                 440                 445
Gly Gly Val Arg Ala Arg Asn Gln Asp Leu Asp Ala Ile Trp Arg Gly
    450                 455                 460
Phe Tyr Ile Ala Gly Asp Pro Ala Leu Ala Tyr Gly Tyr Ala Gln Asp
465                 470                 475                 480
Gln Glu Pro Asp Ala Arg Gly Arg Ile Arg Asn Gly Ala Leu Leu Arg
                485                 490                 495
Val Tyr Val Pro Arg Ser Ser Leu Pro Gly Phe Tyr Arg Thr Ser Leu
            500                 505                 510
Thr Leu Ala Ala Pro Glu Ala Ala Gly Glu Val Glu Arg Leu Ile Gly
        515                 520                 525
```

```
His Pro Leu Pro Leu Arg Leu Asp Ala Ile Thr Gly Pro Glu Glu
    530             535                 540
Gly Gly Arg Leu Glu Thr Ile Leu Gly Trp Pro Leu Ala Glu Arg Thr
545             550                 555                 560
Val Val Ile Pro Ser Ala Ile Pro Thr Asp Pro Arg Asn Ile Gly Gly
                565                 570                 575
Asp Leu Asp Pro Ser Ser Ile Pro Asp Lys Glu Gln Ala Ile Ser Ala
            580                 585                 590
Leu Pro Asp Tyr Ala Ser Gln Pro Gly Lys Pro Pro Lys Asp Glu Leu
            595                 600                 605

<210> SEQ ID NO 4
<211> LENGTH: 94
<212> TYPE: DNA
<213> ORGANISM: Artificial Sequence
<220> FEATURE:
<223> OTHER INFORMATION: Synthetic primer

<400> SEQUENCE: 4
ggtacctatg gagacagaca cactcctgct atgggtactg ctgctctggg ttccaggttc    60
cactggtgac gttatccacg tgaccaagga agtg                              94

<210> SEQ ID NO 5
<211> LENGTH: 27
<212> TYPE: DNA
<213> ORGANISM: Artificial Sequence
<220> FEATURE:
<223> OTHER INFORMATION: Synthetic primer

<400> SEQUENCE: 5
tctagattac agctcgtcct tcggcgg                                       27

<210> SEQ ID NO 6
<211> LENGTH: 54
<212> TYPE: DNA
<213> ORGANISM: Artificial Sequence
<220> FEATURE:
<223> OTHER INFORMATION: Synthetic primer

<400> SEQUENCE: 6
ctgctctggg ttccaggttc cactggtgac gttatccacg tgaccaagga agtg         54

<210> SEQ ID NO 7
<211> LENGTH: 55
<212> TYPE: DNA
<213> ORGANISM: Artificial Sequence
<220> FEATURE:
<223> OTHER INFORMATION: Synthetic primer

<400> SEQUENCE: 7
ggtacctatg gagacagaca cactcctgct atgggtactg ctgctctggg ttcca        55

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ctgtggcatc cacgaaacta                                               20

<210> SEQ ID NO 9
```

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
acatctgctg gaaggtggac                                                    20

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
aggcatcctg accctgaagt ac                                                 22

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
tcttcatgag gtagtctgtc ag                                                 22

<210> SEQ ID NO 12
<211> LENGTH: 18
<212> TYPE: DNA
<213> ORGANISM: Artificial Sequence
<220> FEATURE:
<223> OTHER INFORMATION: Synthetic primer

<400> SEQUENCE: 12
tgtggtcccg tggtgaga                                                      18

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
atcaacaggc tgccaataaa                                                    20
```

B7-1-PE40KDEL EXOTOXIN FUSION GENE-BASED DNA VACCINE AND THE USE THEREOF

CROSS REFERENCE TO RELATED APPLICATIONS

The present application is a 35 U.S.C. §371 national stage patent application of International patent application PCT/CN2011/079862, filed on Sep. 20, 2011, published as WO/2012/094905 on Jul. 19, 2012, the text of which is incorporated by reference, and claims the benefit of the filing date of Chinese application no. 201110023985.6, filed on Jan. 14, 2011, the text of which is also incorporated by reference.

FIELD OF THE INVENTION

The present invention relates to the fields of immunology and molecular biology and is related to a B7-1-PE40KDEL exotoxin fusion gene-based DNA vaccine and the use thereof. The invention also relates to a B7-1-PE40KDEL exotoxin fusion gene, an exotoxin fusion protein encoded by the fusion gene, a recombinant expression vector containing the fusion gene, and a composition that contain the recombinant expression vector.

BACKGROUND OF THE INVENTION

Allogeneic hematopoietic stem cell transplantation (allo-HSCT) and solid organ transplantation have been widely used in the treatment of hematologic malignancies, certain genetic diseases, acute severe radiation sickness, and a variety of solid organ failures and malignancies. Due to the differences in the major histocompatibility antigen (MHC) between donors and recipients, along with many other known and unknown factors such as the minor histocompatibility antigen (mHA), tissue-specific antigens, and non-immunological factors, host-versus-graft diseases (HVGDs) and graft-versus-host diseases (GVHDs or GVHRs) are inevitable and are one of the most important and fundamental causes of allogeneic tissue graft failure and graft chronic dysfunction (GCD). With the increasing number of patients in urgent need of organ transplants, the lack of donors is increasingly prominent. Both now and in the future, transplant cases in which the MHCs are not fully compatible or are only semi-compatible will become mainstream and constitute the new direction of hematopoietic stem cell transplantation and organ transplantation. The traditional methods for the prevention and treatment of GVHD and HVGD are based on the destruction of the entire immune function in transplant recipients, even at the cost of the loss of graft-versus-leukemia (GVL) and anti-inflammatory functions, implemented by the use of a variety of high-dose immunosuppressants or the removal of all T cells from the graft. There is no doubt that the fundamental method behind any new strategy to prevent the occurrence and development of GVHD and HVGD depends on whether the initial step of T cell activation can be effectively interfered with or inhibited to induce specific immune tolerance, thereby fundamentally curbing the occurrence and development of a "cytokine storm". Therefore, an ideal and efficient allo-HSCT and organ transplantation should amend or modify the initial reaction of T cells to allogeneic antigens rather than removing all T cells from the body of the transplant recipient or the donor graft. That is, the induction of recipient or donor-specific immune tolerance should target the elimination or inhibition of the recipient or donor T-cell reaction to allogeneic antigens but still retain the normal reaction of T cells to other antigens.

It has been proven that the recipient and donor T cells play a dual role in hematopoietic stem cell transplantation or organ transplantation. In addition to contributing to the engraftment of hematopoietic stem cells or organs and control conditional infections and anti-leukemia effects, they can also be the root cause of GVHD or HVGD. This immune response is accomplished through recognition and activation by T cells. T cell activation requires two signals: T cell receptor signal and co-stimulation signal of cluster of differentiation 28 (CD28). The first signal is regulated by the second signal, resulting in T cell activation, partial activation or anergy. Therefore, inhibiting T cell activation by blocking either the T cell receptor signal or the CD28-mediated co-stimulatory signal is an important strategy for the prevention of HVGD and acute GVHD (aGVHD). The cytotoxic T-lymphocyte antigen 4-Ig (CTLA4-Ig) or B7 antibody-induced specific immune tolerance is primarily used to achieve the goal of preventing HVGD and aGVHD and has been proven effective in a large number of in vivo and in vitro animal experiments. However, the shortcomings of this method are that the duration of the induced immune tolerance is short and that the induced incompetent T cells can be reactivated by other signaling pathways, leading to treatment failure. In addition, the monoclonal antibodies used for blocking are mostly murine, and their immunogenicity will affect the treatment's efficacy.

Therefore, a DNA vaccine with good immune tolerance and therapeutic efficacy for the treatment or the prevention of allogeneic tissue/organ transplant rejection such as GVHD is urgently needed in this field.

SUMMARY OF THE INVENTION

After numerous experiments and creative work, the inventors have discovered a B7-1-PE40KDEL exotoxin fusion gene and, surprisingly, found that the recombinant expression vector pcDNA3.1/Zeo(+)-B7-1-PE40KDEL that is transfected into eukaryotic cells is transcribed, translated, post-translationally modified, and then secreted into the extracellular space. The vector pcDNA3.1/Zeo(+)-B7-1-PE40KDEL can be efficiently expressed in eukaryotic cells, and the expression product has good targeting immunosuppressive activity. The inventors have also found that the pcDNA3.1/Zeo(+)-B7-1-PE40KDEL exotoxin fusion gene-based DNA vaccine can be effective in the prevention and treatment in murine aGVHD model. Therefore, the following invention is provided.

One aspect of the invention relates to a B7-1-PE40KDEL exotoxin fusion gene, and its nucleotide sequence is shown as SEQ ID NO: 1 or SEQ ID NO: 2.
The determination of the B7-1-PE40KDEL sequence and the open reading frame are analyzed as follows:
The nucleotide sequence of SEQ ID NO: 1 (1850 base pairs [bp]):

```
CGTTTAACTT AAGCTTGGTA CCTATGGAGA CAGACACACT CCTGCTATGG GTACTGCTGC    60
TCTGGGTTCC AGGTTCCACT GGTGACGTTA TCCACGTGAC CAAGGAAGTG AAAGAAGTAG   120
```

-continued

```
CAACGCTGTC CTGTGGTCAC AATGTTTCTG TTGAAGAGCC GGCACAAACT CGCATCTACT  180
GGCAAAAGGA GAAGAAAATG GTGCTGACTA TGATGTCTGG GGACATGAAT ATATGGCCCG  240
AGTACAAGAA CCGGACCATC TTTGATATTA CTAATAACCT CTCCATTGTG ATCCTGGCTC  300
TGCGCCCATC TGACGAGGGC ACATACGAGT GTGTTGTTCT GAAGTATGAA AAAGACGCTT  360
TCAAGCGGGA ACACCTGGCT GAAGTGACGT TATCAGTCAA AGCTGACTTC CCTACACCTA  420
GTATATCTGA CTTTGAAATT CCAACTTCTA ATATTAGAAG GATAATTTGC TCAACCTCTG  480
GAGGTTTTCC AGAGCCTCAC CTCTCCTGGT TGGAAAATGG AGAAGAATTA AGTGCCATCA  540
ACACAACAGT TTCCCAAGAT CCTGAAACTG AGCTCTATGC TGTTAGCAGC AAACTGGATT  600
TCAATATGAC AACCAACCAC AGCTTCATGT GTCTCATCAA GTATGGACAT TTAAGAGTGA  660
ATCAGACCTT CAACTGGAAT ACAACCAAGC AAGAGCATTT TCCTGATAAC GGTGGCGGCG  720
GATCTGGAGG CGGTGGAAGC GGTGGTGGCT CGGGCGGTGG TGGGTCGGGC GGCAGCCTGG  780
CCGCGCTGAC CGCGCACCAG GCTTGCCACC TGCCGCTGGA GACTTCCACC CGTCATCGCC  840
AGCCGCGCGG CTGGGAACAA CTGGAGCAGT GCGGCTATCC GGTGCAGCGG CTGGTCGCCC  900
TCTACCTGGC GGCGCGGCTG TCGTGGAACC AGGTCGACCA GGTGATCCGC AACGCCCTGG  960
CCAGCCCCGG CAGCGGCGGC GACCTGGGCG AAGCGATCCG CGAGCAGCCG GAGCAGGCCC 1020
GTCTTGCCCT GACCCTGGCC GCCGCCGAGA GCGAGCGCTT CGTCCGGCAG GGCACCGGCA 1080
ACGACGAGGC CGGCGCGGCC AACGCCGACG TGGTGAGCCT GACCTGCCCG GTCGCCGCCG 1140
GTGAATGCGC GGGCCCGGCG GACAGCGGCG ACGCCCTGCT GGAGCGCAAC TATCCCACTG 1200
GCGCGGAGTT CCTCGGCGAC GGCGGCGACG TCAGCTTCAG CACCCGCGGC ACGCAGAACT 1260
GGACGGTGGA GCGGCTGCTC CAGGCGCACC GCCAACTGGA GGAGCGCGGC TATGTGTTCG 1320
TCGGCTACCA CGGCACCTTC CTCGAAGCGT CGCAAAGCAT CGTCTTCGGC GGGGTGCGCG 1380
CGCGCAACCA GGACCTCGAC GCGATCTGGC GCGGTTTCTA TATCGCCGGC GATCCGGCGC 1440
TGGCCTACGG CTACGCCCAG GACCAGGAAC CCGACGCACG CGGCCGGATC CGCAACGGTG 1500
CCCTGCTGCG GGTCTATGTG CCGCGCTCGA GCCTGCCGGG CTTCTACCGC ACCAGCCTGA 1560
CCCTGGCCGC GCCGGAGGCG GCGGGCGAGG TCGAACGGCT GATCGGCCAT CCGCTGCCGC 1620
TGCGCCTGGA CGCCATCACC GGCCCCGAGG AGGAAGGCGG GCGCCTGGAG ACCATTCTCG 1680
GCTGGCCGCT GGCCGAGCGC ACCGTGGTGA TTCCCTCGGC GATCCCCACC GACCCGCGCA 1740
ACATCGGCGG CGACCTCGAC CCGTCCAGCA TCCCCGACAA GGAACAGGCG ATCAGCGCCC 1800
TGCCGGACTA CGCCAGCCAG CCCGGCAAAC CGCCGAAGGA CGAGCTCTAA            1850
```

In the above sequence, the underlined parts are Kpn I restriction sites, and the framed parts are the start codon and stop codon. The open reading frame of the above sequence SEQ ID NO: 1 is SEQ ID NO: 2 (1827 bp).

Another aspect of the invention relates to the exotoxin fusion protein (SEQ ID NO: 3) encoded by the exotoxin fusion gene (SEQ ID NO: 1 or SEQ ID NO: 2).

The amino acid sequence of SEQ ID NO: 3 is shown as follows: (608 amino acids, the underlined part is the signal peptide sequence).

```
Met Glu Thr Asp Thr Leu Leu Leu Trp Val Leu Leu Leu Trp Val Pro
1               5                   10                  15

Gly Ser Thr Gly Asp Val Ile His Val Thr Lys Glu Val Lys Glu Val
            20                  25                  30

Ala Thr Leu Ser Cys Gly His Asn Val Ser Val Glu Glu Pro Ala Gln
        35                  40                  45
```

-continued

```
Thr Arg Ile Tyr Trp Gln Lys Glu Lys Lys Met Val Leu Thr Met Met
 50                  55                  60

Ser Gly Asp Met Asn Ile Trp Pro Glu Tyr Lys Asn Arg Thr Ile Phe
 65                  70                  75                  80

Asp Ile Thr Asn Asn Leu Ser Ile Val Ile Leu Ala Leu Arg Pro Ser
                 85                  90                  95

Asp Glu Gly Thr Tyr Glu Cys Val Val Leu Lys Tyr Glu Lys Asp Ala
                100                 105                 110

Phe Lys Arg Glu His Leu Ala Glu Val Thr Leu Ser Val Lys Ala Asp
            115                 120                 125

Phe Pro Thr Pro Ser Ile Ser Asp Phe Glu Ile Pro Thr Ser Asn Ile
        130                 135                 140

Arg Arg Ile Ile Cys Ser Thr Ser Gly Gly Phe Pro Glu Pro His Leu
145                 150                 155                 160

Ser Trp Leu Glu Asn Gly Glu Glu Leu Ser Ala Ile Asn Thr Thr Val
                165                 170                 175

Ser Gln Asp Pro Glu Thr Glu Leu Tyr Ala Val Ser Ser Lys Leu Asp
            180                 185                 190

Phe Asn Met Thr Thr Asn His Ser Phe Met Cys Leu Ile Lys Tyr Gly
        195                 200                 205

His Leu Arg Val Asn Gln Thr Phe Asn Trp Asn Thr Thr Lys Gln Glu
    210                 215                 220

His Phe Pro Asp Asn Gly Gly Gly Ser Gly Gly Gly Ser Gly
225                 230                 235                 240

Gly Gly Ser Gly Gly Gly Ser Gly Gly Ser Leu Ala Ala Leu Thr
                245                 250                 255

Ala His Gln Ala Cys His Leu Pro Leu Glu Thr Ser Thr Arg His Arg
            260                 265                 270

Gln Pro Arg Gly Trp Glu Gln Leu Glu Gln Cys Gly Tyr Pro Val Gln
        275                 280                 285

Arg Leu Val Ala Leu Tyr Leu Ala Ala Arg Leu Ser Trp Asn Gln Val
290                 295                 300

Asp Gln Val Ile Arg Asn Ala Leu Ala Ser Pro Gly Ser Gly Gly Asp
305                 310                 315                 320

Leu Gly Glu Ala Ile Arg Glu Gln Pro Glu Gln Ala Arg Leu Ala Leu
                325                 330                 335

Thr Leu Ala Ala Ala Glu Ser Glu Arg Phe Val Arg Gln Gly Thr Gly
            340                 345                 350

Asn Asp Glu Ala Gly Ala Ala Asn Ala Asp Val Val Ser Leu Thr Cys
        355                 360                 365

Pro Val Ala Ala Gly Glu Cys Ala Gly Pro Ala Asp Ser Gly Asp Ata
    370                 375                 380

Leu Leu Glu Arg Asn Tyr Pro Thr Gly Ala Glu Phe Leu Gly Asp Gly
385                 390                 395                 400

Gly Asp Val Ser Phe Ser Thr Arg Gly Thr Gln Asn Trp Thr Val Glu
                405                 410                 415

Arg Leu Leu Gln Ala His Arg Gln Leu Glu Glu Arg Gly Tyr Val Phe
            420                 425                 430

Val Gly Tyr His Gly Thr Phe Leu Glu Ala Ala Gln Ser Ile Val Phe
        435                 440                 445

Gly Gly Val Arg Ala Arg Asn Gln Asp Leu Asp Ala Ile Trp Arg Gly
    450                 455                 460

Phe Tyr Ile Ala Gly Asp Pro Ala Leu Ala Tyr Gly Tyr Ala Gln Asp
465                 470                 475                 480
```

-continued

```
Gln Glu Pro Asp Ala Arg Gly Arg Ile Arg Asn Gly Ala Leu Leu Arg
            485                 490                 495

Val Tyr Val Pro Arg Ser Ser Leu Pro Gly Phe Tyr Arg Thr Ser Leu
            500                 505                 510

Thr Leu Ala Ala Pro Glu Ala Ala Gly Glu Val Glu Arg Leu Ile Gly
        515                 520                 525

His Pro Leu Pro Leu Arg Leu Asp Ala Ile Thr Gly Pro Glu Glu Glu
    530                 535                 540

Gly Gly Arg Leu Glu Thr Ile Leu Gly Trp Pro Leu Ala Glu Arg Thr
545                 550                 555                 560

Val Val Ile Pro Ser Ala Ile Pro Thr Asp Pro Arg Asn Ile Gly Gly
            565                 570                 575

Asp Leu Asp Pro Ser Ser Ile Pro Asp Lys Glu Gln Ala Ile Ser Ala
            580                 585                 590

Leu Pro Asp Tyr Ala Ser Gln Pro Gly Lys Pro Pro Lys Asp Glu Leu
    595                 600                 605
```

Another aspect of the invention relates to a recombinant expression vector containing the B7-1-PE40KDEL exotoxin fusion gene that can be effectively fused with selected eukaryotic expression vectors, such as pcDNA3.1/Zeo(+), pWL-NEO, pSV2CAT, pOG44, pXT1, pSG, pSVK3, pBPV, pMSG, pSVL, and adenoviruses.

In one aspect of the invention, the recombinant expression vector consists of the B7-1-PE40KDEL gene and pcDNA3.1/Zeo(+) vector.

Another aspect of the invention relates to a composition containing any of the recombinant expression vectors in the invention.

The invention also relates to a DNA vaccine for the treatment or prevention of GVHD, which includes any of the recombinant expression vectors in the invention.

In one aspect of the invention, DNA vaccine described herein also includes pharmaceutically acceptable immune adjuvants.

In another aspect of the invention, DNA vaccine described herein is used for immunization via injection or mucosal or gene gun transfer. Specifically, DNA vaccine is used for immunization via at least one of the following methods: intravenous injection, intraarterial injection, intramuscular injection, subcutaneous injection, organ injection, pleural injection, and intraperitoneal injection.

In another aspect of the invention, the DNA vaccine described herein can be in the form of either an aqueous solution or a reconstituted freeze-dried powder used for injection or administration via the mucosae.

Another aspect of the invention relates to a method of DNA vaccine preparation, including the procedures to effectively fuse the B7-1-PE40 exotoxin fusion gene containing the SEQ ID NO: 1 or 2 nucleotide sequence and the pcDNA3.1/Zeo(+) vector.

The methods of DNA vaccine preparation described herein according to the invention include the following steps:

1) An upstream primer (P1) that contains the signal peptide and Kpn I restriction sites and a downstream primer (P2) that contains the Xba I restriction sites are designed. The primer sequences described are shown as SEQ ID NO: 4 and SEQ ID NO: 5.

2) The prokaryotic expression vector pGEMT-B7-1-PE40KDEL is used as the template for polymerase chain reaction (PCR) amplification using high-fidelity Pfu DNA polymerase.

3) PCR products are recovered. The recovered PCR product and the pcDNA3.1/Zeo(+) vector are double-digested with Kpn I+Xba 1 restriction enzymes, and the digested products are recovered after electrophoresis.

4) The digested products are recovered.

5) The double-digested PCR product and the pcDNA3.1/Zeo(+) vector are ligated.

6) Ampicillin-resistant bacterial clones are selected, and plasmids are extracted and identified by double digestion with restriction enzymes. The correct bacterial clones are cryopreserved.

7) The bacterial clone is cultured, and plasmids for DNA vaccine are extracted and purified.

8) The obtained plasmids are mixed with pharmaceutically acceptable immune adjuvants.

Another aspect of the invention relates to the exotoxin fusion gene or the application of the recombinant expression vector in the preparation of a DNA vaccine for the treatment or prevention of GVHD.

An additional aspect of the invention relates to the methods for the treatment or prevention of GVHD, including the steps of administering the effective treatment or prevention doses of a DNA vaccine to the subject.

The daily dose can be administered to the subject all at once or can also be administered in two, three, four, or more smaller doses at appropriate intervals over the course of a day. Smaller doses described herein may be prepared as unit doses, for example, each unit dose contains the dose that corresponds to the total daily dose divided by the number of appropriate doses. Additionally, DNA vaccine can also be administered at a certain interval: once a day, once every two days, once a week, once a month, once every two months, once every three months, once every six months, once a year, or once every two years.

BRIEF DESCRIPTION OF THE DRAWINGS

FIG. 1. The schematic representation of construction of eukaryotic expression vector pcDNA3.1/B7-1-PE40KDEL, in which S indicates the signal peptide sequence.

FIG. 2. Agarose gel electrophoresis analysis of B7-1-PE40KDEL PCR products. Lane 1, DNA marker; Lane 2, B7-1-PE40KDEL PCR products.

FIG. 3. Agarose gel electrophoresis analysis of double-digested recombinant plasmid pcDNA3.1/B7-1-PE40KDEL was double-digested with Kpn I+Xba I restriction enzymes. Lane 1, DNA marker; Lane 2, Xba I-digested recombinant plasmid; Lane 3, Kpn I+Xba I double-digested recombinant plasmid.

Figure 4:
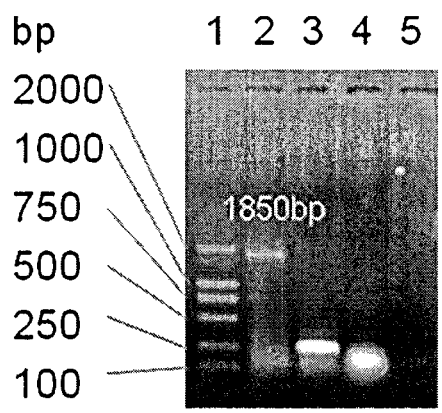

FIG. 4. Agarose gel electrophoresis analysis of reverse transcriptase-PCR (RT-PCR) products of transfected CHO-K1-RPE.40 cells. Lane 1, DNA marker; Lane 2, B7-1-PE40KDEL amplification products in pcDNA3.1/B7-1-PE40KDEL-transfected CHO-K1-RPE.40 cells; Lane 3, β-actin PCR products; Lane 4, B7-1-PE40KDEL amplification products in pcDNA3.1 empty vector-transfected CHO-K1-RPE.40 cells; Lane 5, B7-1-PE40KDEL amplification products in untransfected CHO-K1-RPE.40 cells.

Figure 5:
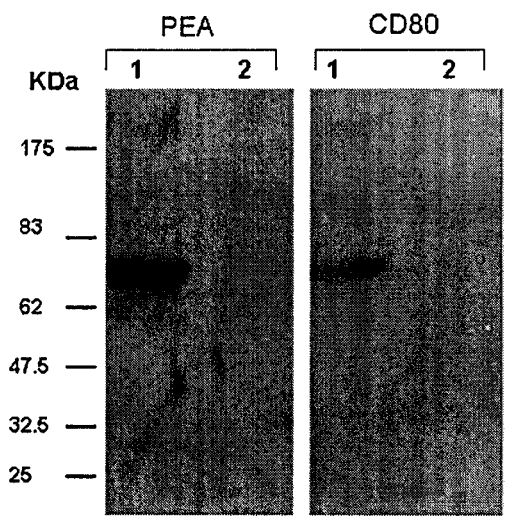

FIG. 5. Western blot analysis of B7-1-PE40KDEL fusion protein secreted from transfected eukaryotic cells. Lane 1, transfected with pcDNA3.1/Zeo(+)-B7-1-PE40KDEL; Lane 2, transfected with pcDNA3.1/Zeo(+) empty vector.

Figure 6:
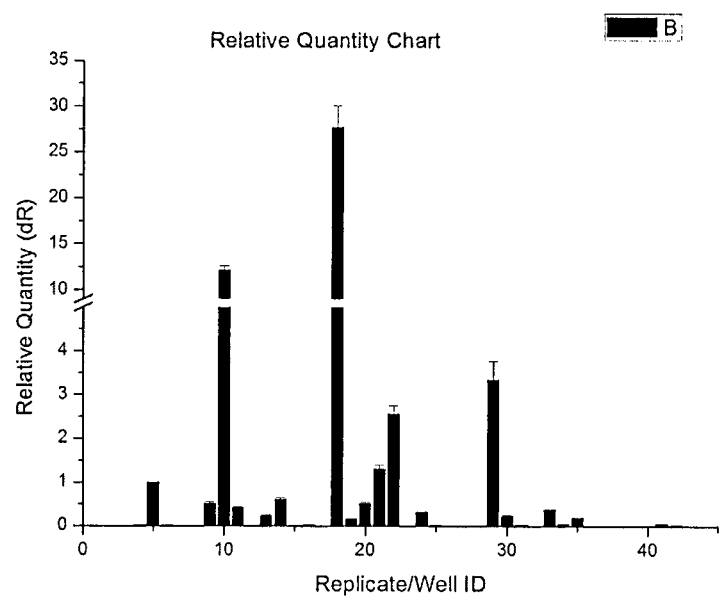
Figure 6:
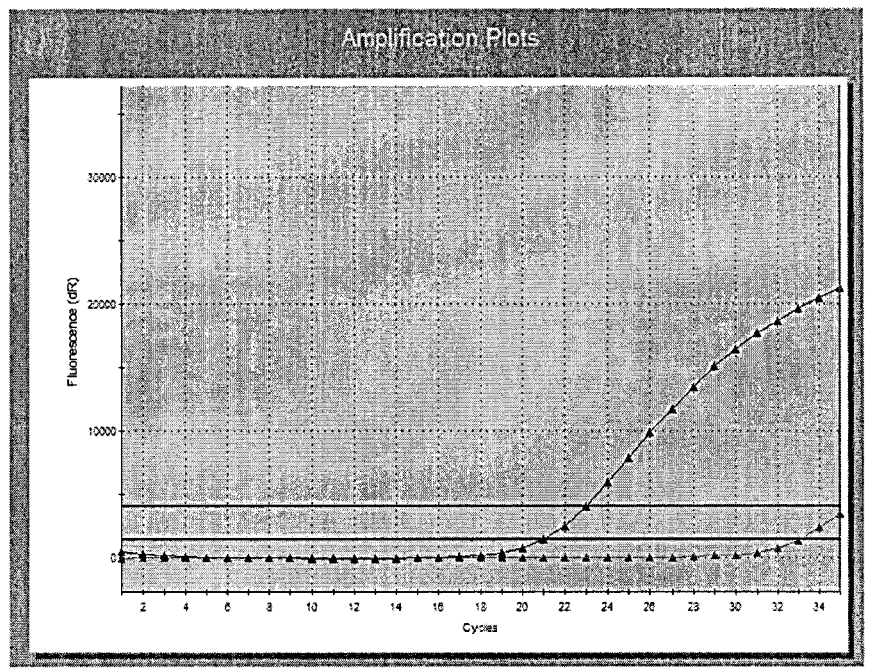
Figure 6:
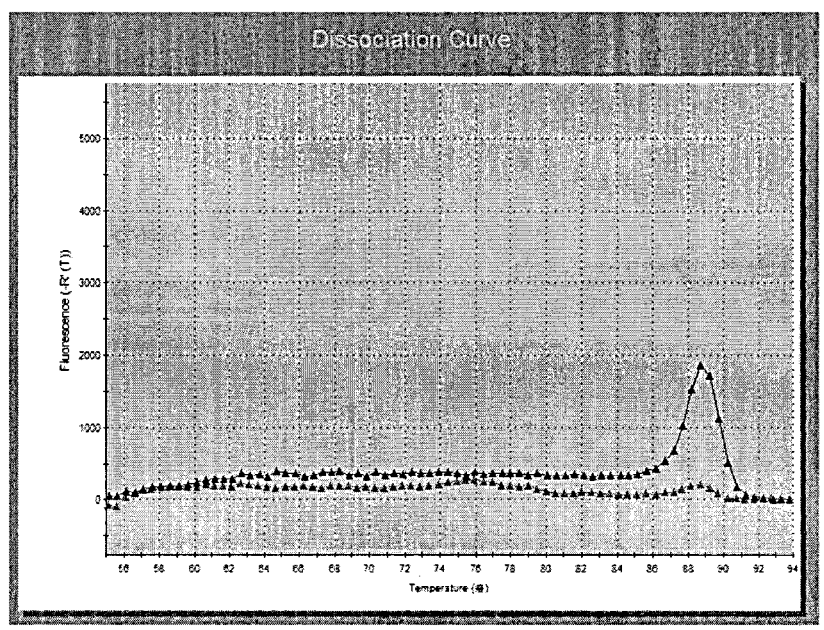

FIG. 6. Relative quantitative results of *Pseudomonas* exotoxin A (PEA) expression in stably transfected CHO-K1-RPE.40 with Zeo screening. A, real-time quantitative PCR; B, amplification curve; C, solubility curve.

Figure 7:
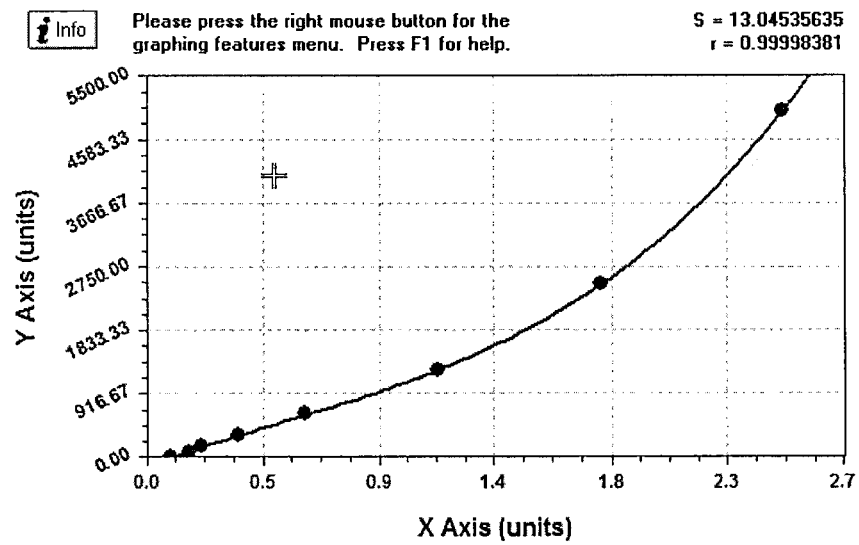

FIG. 7. Standard curve of the measurement of PEA concentration.

Figure 8:
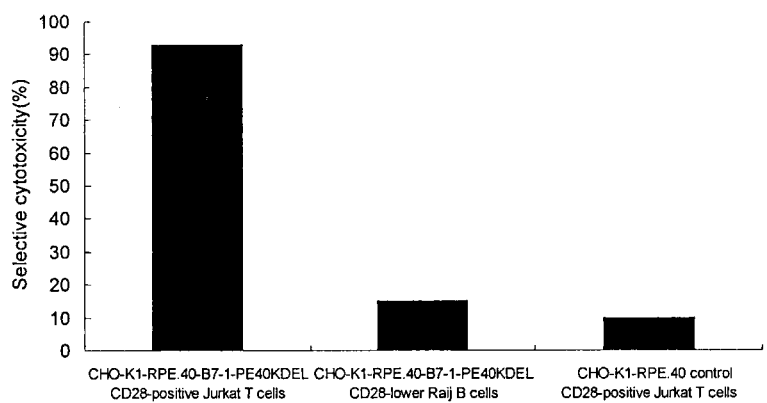

FIG. 8. Comparison of the selective inhibitory activity of eukaryotic expression products B7-1-PE40KDEL.

Figure 9:
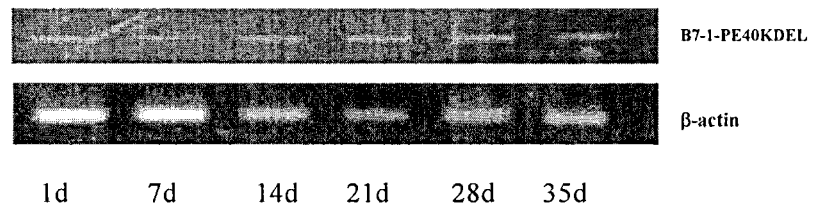

FIG. 9. Agarose gel electrophoresis analysis of the serum expression level of pcDNA3.1/B7-1-PE40KDEL plasmid after intramuscular injection.

Figure 10:
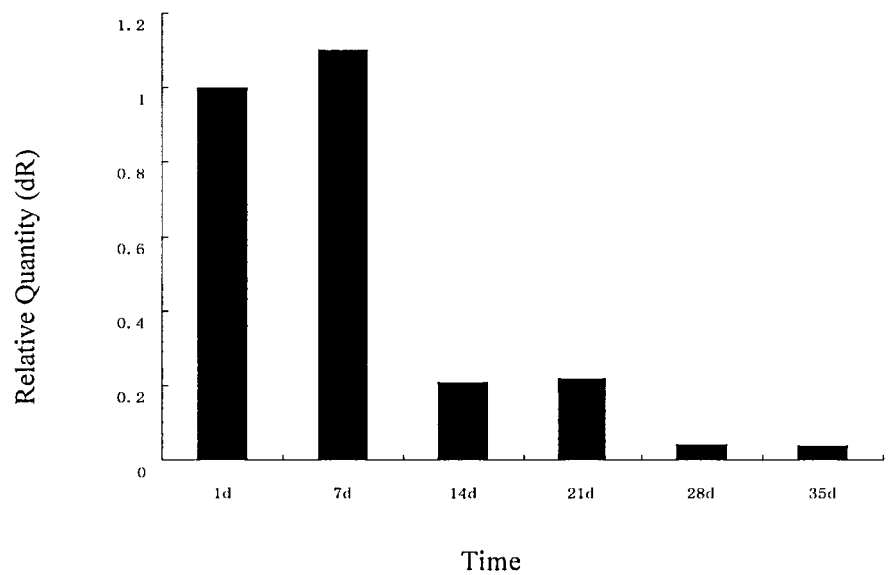
Figure 11A:
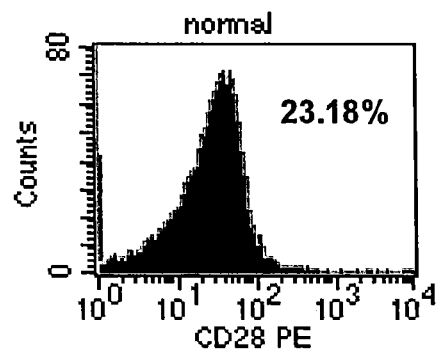
Figure 11B:
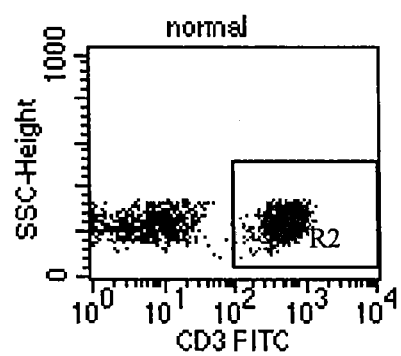
Figure 11C:
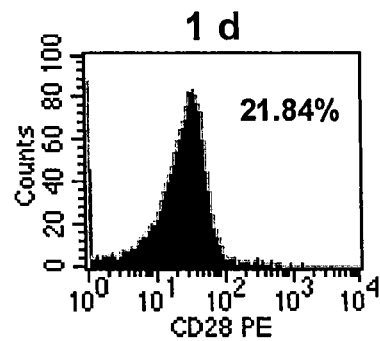
Figure 11D:
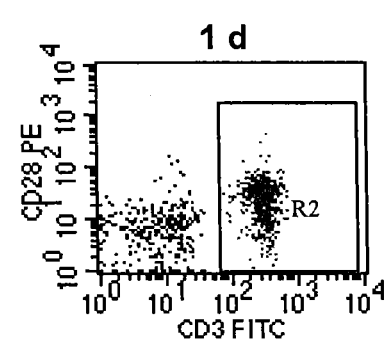
Figure 11E:
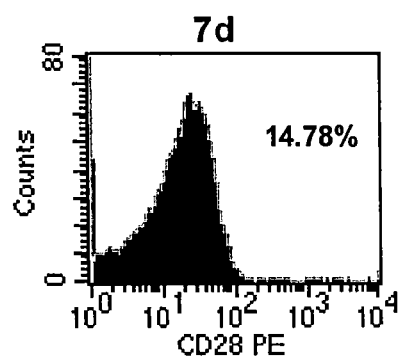
Figure 11F:
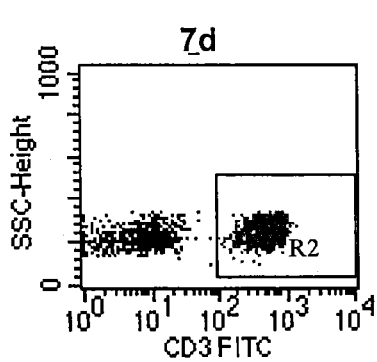
Figure 11G:
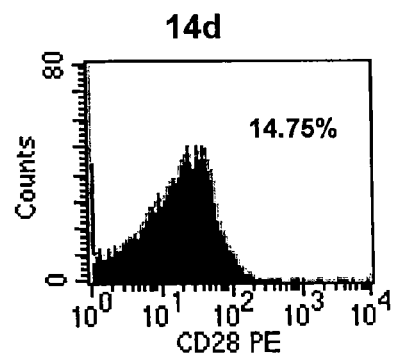
Figure 11H:
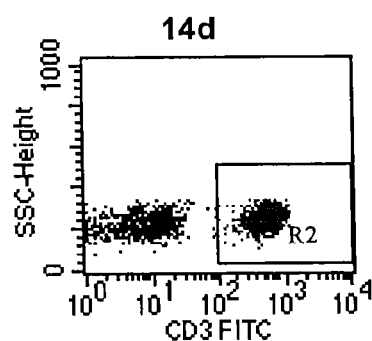
Figure 11I:
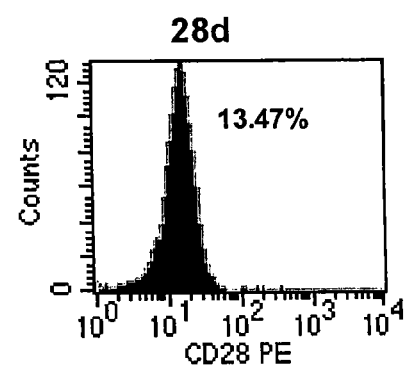
Figure 11J:
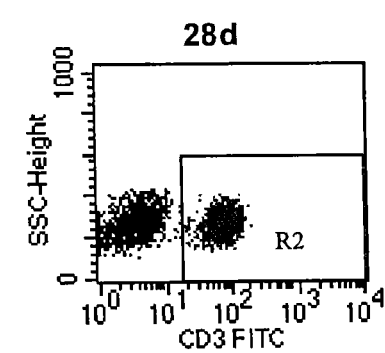
Figure 11K:
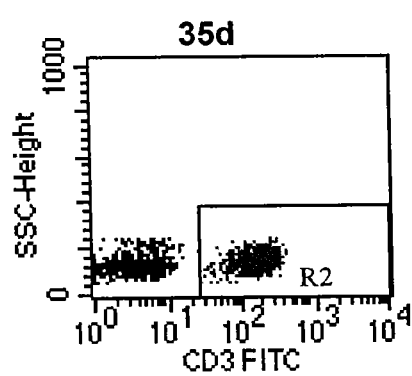
Figure 11L:
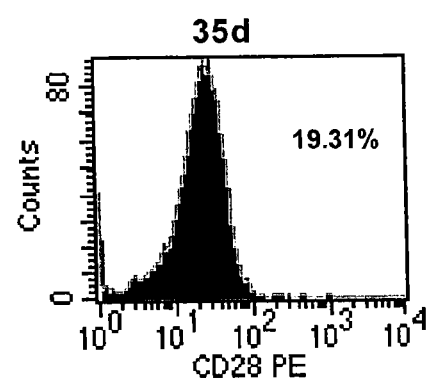

FIG. 10. Relative quantitative PE40KDELmRNA in blood.

FIGS. 11A through L. Representative photos of flow cytometric analysis of $CD3^+CD28^+T$ counts in peripheral blood.

Figure 12:
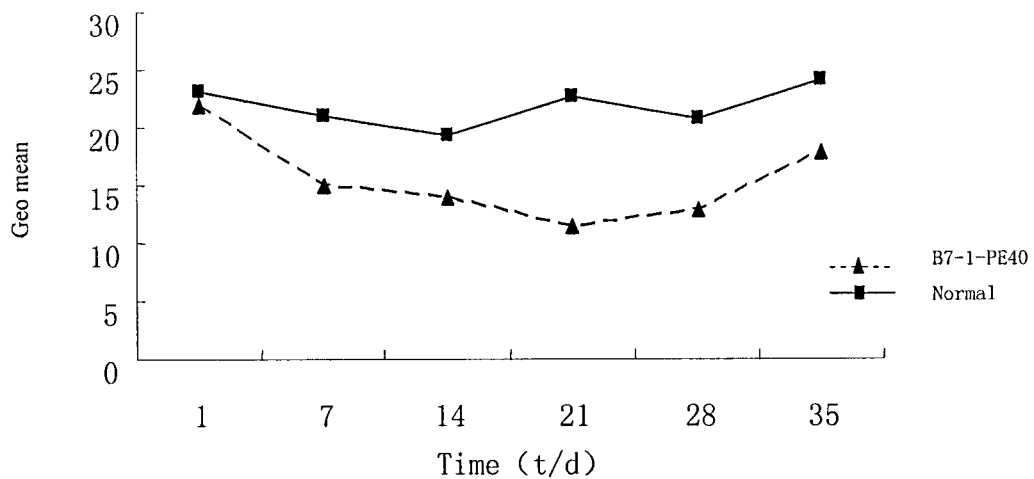

FIG. 12. The reduction of peripheral blood $CD28^+T$ cells after an intramuscular injection of B7-1-PE40KDEL DNA vaccines.

Figure 13:
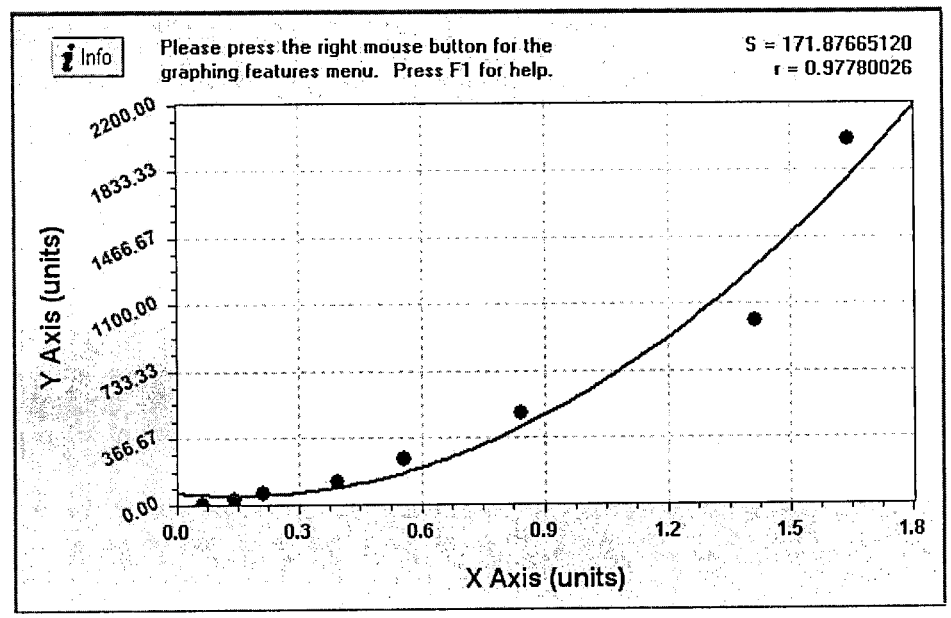

FIG. 13. Standard curve of the measurement of the serum Anti-PEA IgG antibody concentration.

Figure 14:
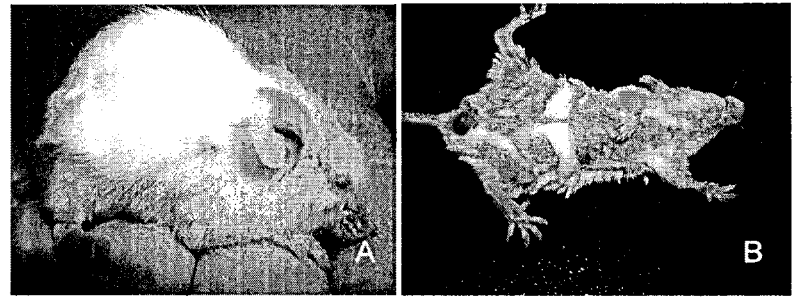

FIG. 14. Typical GVHD symptoms in recipient mice. Typical hunched posture (A) and epilation (B).

Figure 15:
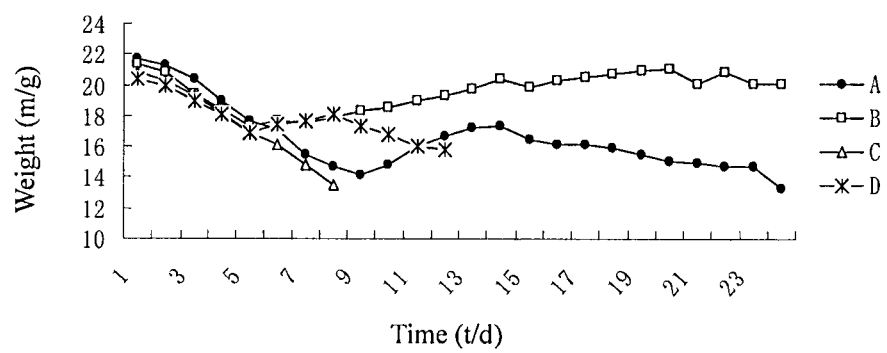

FIG. 15. The changes in mice body weight in all groups after transplantation. A, aGVHD model group; B, Bone marrow transplantation group; C, Spleen cell infusion group; D, Radiation group alone.

Figure 16:
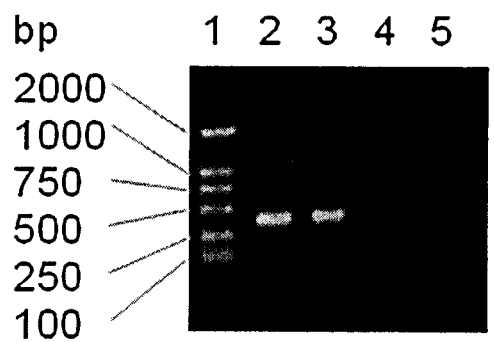

FIG. 16. Chimerism analysis after transplantation: electrophoresis of the PCR products of sex-determining region Y (sry gene in Y chromosome). Lane 1, DNA marker; Lane 2, sry gene amplification in aGVHD model group; Lane 3, sry gene amplification in bone marrow transplantation group; Lane 4, sry gene amplification in spleen cell infusion group; Lane 5, sry gene amplification in radiation group alone.

Figure 17:
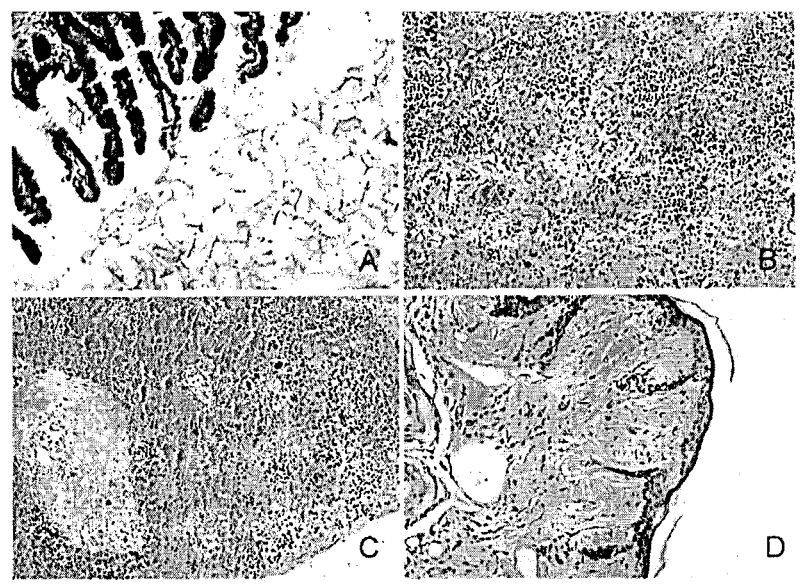

FIG. 17. Histopathological examinations of aGVHD mice (hematoxylin and eosin [HE] staining×100). A, Small intestine; B, Liver; C, Spleen; D, Skin.

Figure 18:
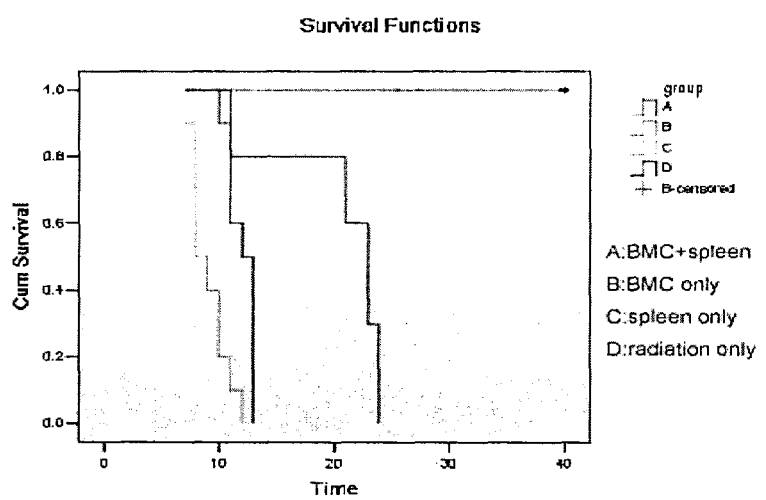

FIG. 18. The survival rates of GVHD mice in all groups after transplantation.

Figure 19:
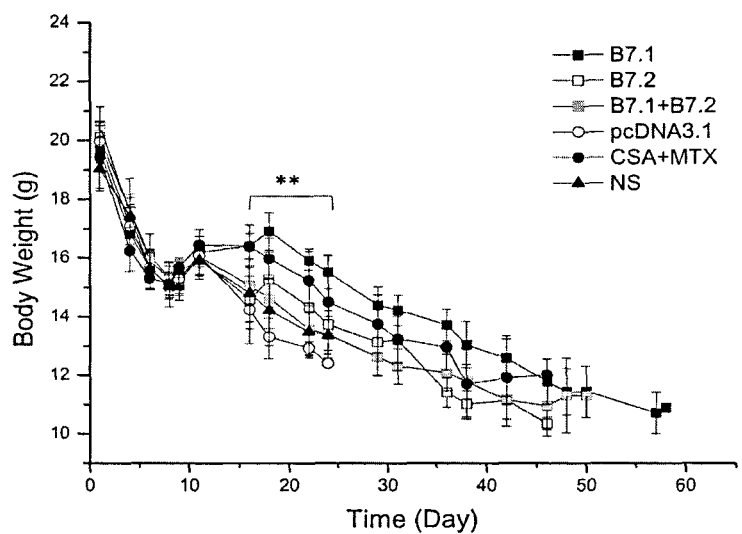

FIG. 19. The changes in body weight in GVHD mice in all groups after transplantation.

Figure 20:
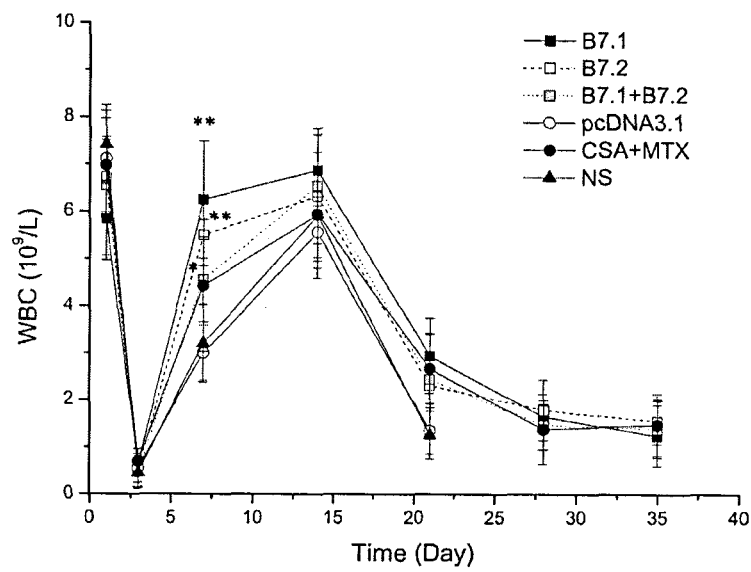

FIG. 20. The change in white blood cell (WBC) counts in aGVHD mice in all groups after transplantation.

Figure 21:
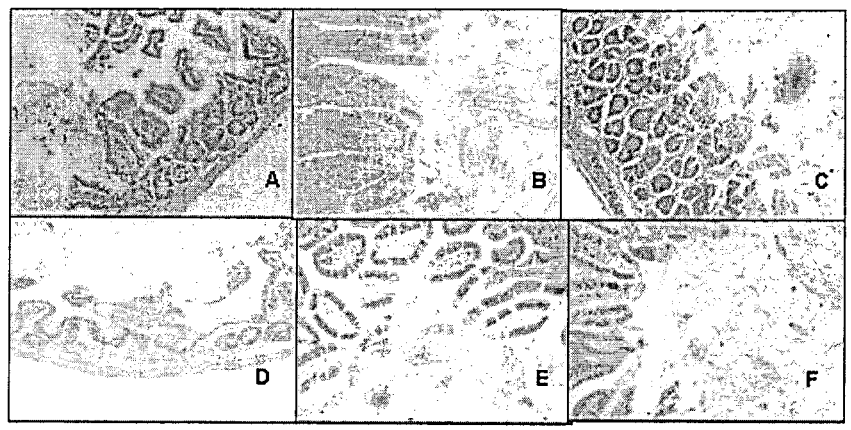

FIG. 21. Histopathological changes in the small intestines of aGVHD mice in all groups after treatment with B7-1-PE40KDEL DNA vaccine and B7-2-PE40KDEL DNA vaccines (HE staining, 40×): A group (B7-1-PE40KDEL DNA vaccine), B group (B7-2-PE40KDEL DNA vaccine), C group (B7-1-PE40KDEL DNA vaccine+B7-2-PE40KDEL DNA vaccine), D group (empty vector), E group (cyclosporin A [CsA]+methotrexate [MTX]) and F group (untreated aGVHD group).

Figure 22:
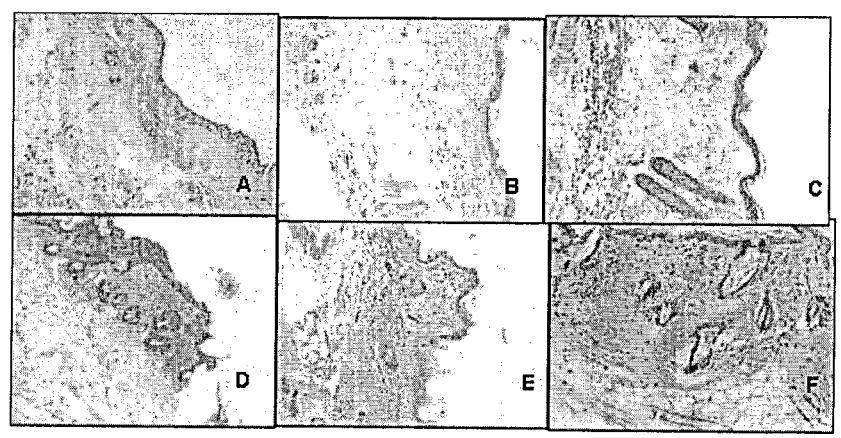

FIG. 22. Histopathological changes in the skin of aGVHD mice in all groups after treatment with B7-1-PE40KDEL DNA vaccine and B7-2-PE40KDEL DNA vaccines (HE staining, 40×): A group (B7-1-PE40KDEL DNA vaccine), B group (B7-2-PE40KDEL DNA vaccines), C group (B7-1-PE40KDEL+B7-2-PE40KDEL DNA vaccines), D group (empty vector), E group (CsA+MTX) and F group (untreated aGVHD group).

Figure 23:
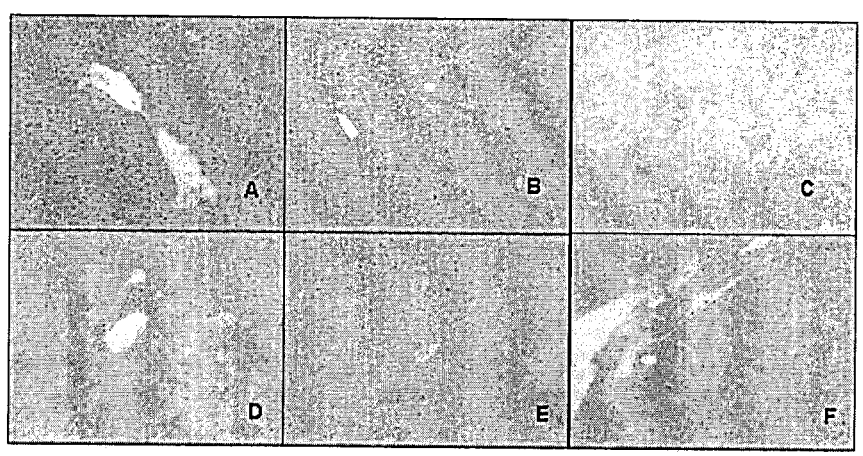

FIG. 23. Histopathological changes in the livers of aGVHD mice in all groups after treatment with B7-1-PE40KDEL DNA vaccine and B7-2-PE40KDEL DNA vaccine (HE staining, 40×): A group (B7-1-PE40KDEL DNA vaccine), B group (B7-2-PE40KDEL DNA vaccine), C group (B7-1-PE40KDEL DNA vaccine+B7-2-PE40KDEL DNA vaccine), D group (empty vector), E group (CsA+MTX) and F group (untreated aGVHD group).

Figure 24:
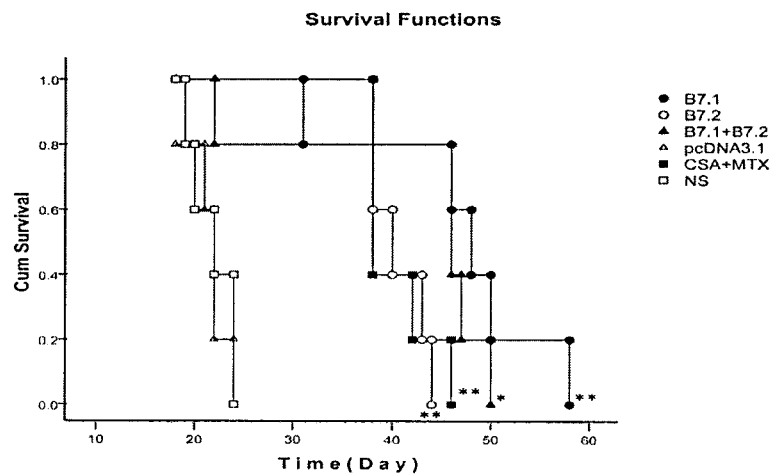

FIG. 24. The survival curves and median survival times of aGVHD mice in all groups after treatment with B7-1-PE40KDEL and B7-2-PE40KDEL DNA vaccines.

Figure 25:
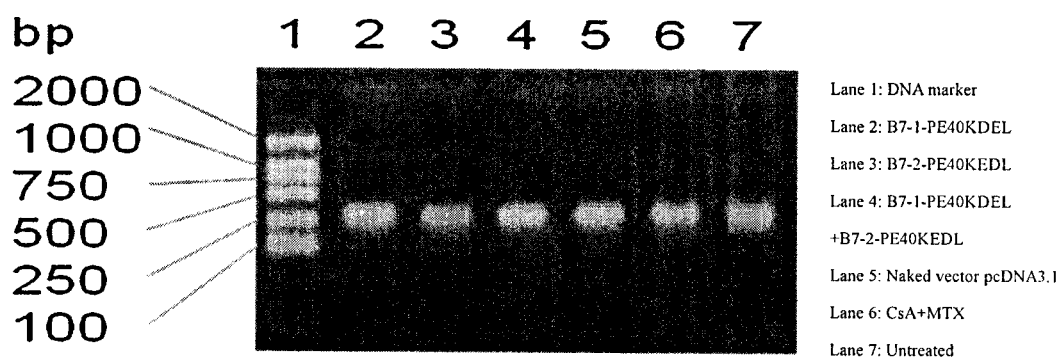

FIG. 25. Chimerism analysis in all groups after transplantation: Electrophoresis of the sry gene (Y chromosome) PCR products. Lane 1, DNA marker; Lane 2, sry gene amplification in B7-1-PE40KDEL DNA vaccine group; Lane 3, sry gene amplification in B7-2-PE40KDEL DNA vaccine group; Lane 4, sry gene amplification in B7-1-PE40KDEL+B7-2-PE40KDEL DNA vaccines group; Lane 5, sry gene amplification in the pcDNA3.1 infusion group; Lane 6, sry gene amplification in CsA+MTX group; Lane 7, sry gene amplification in aGVHD model group.

Figure 26:
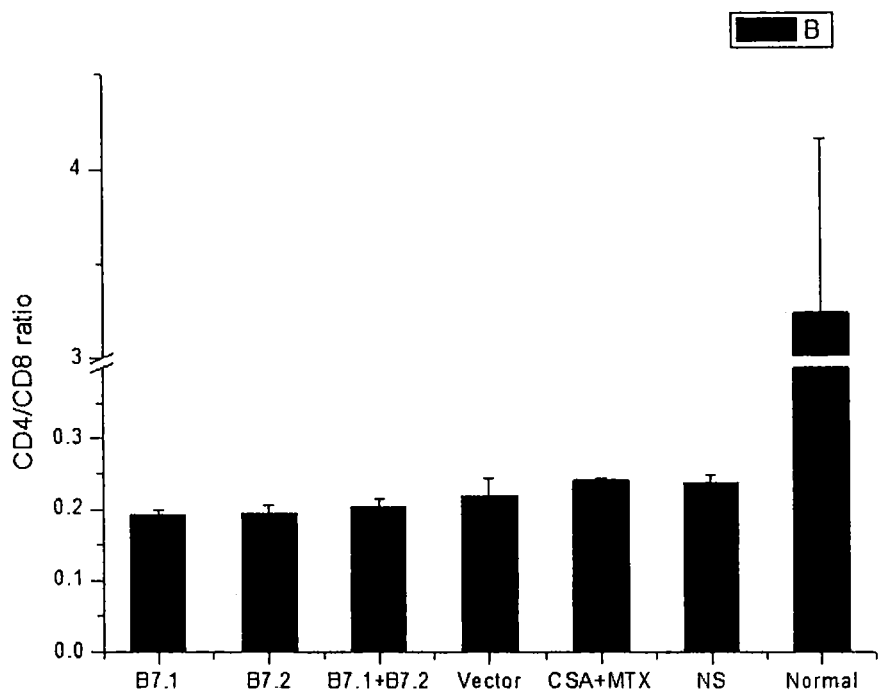

FIG. 26. The effect of DNA vaccine on $CD4^+/CD8^+$ ratio of peripheral blood in aGVHD mice.

Figures 27A, 27B:
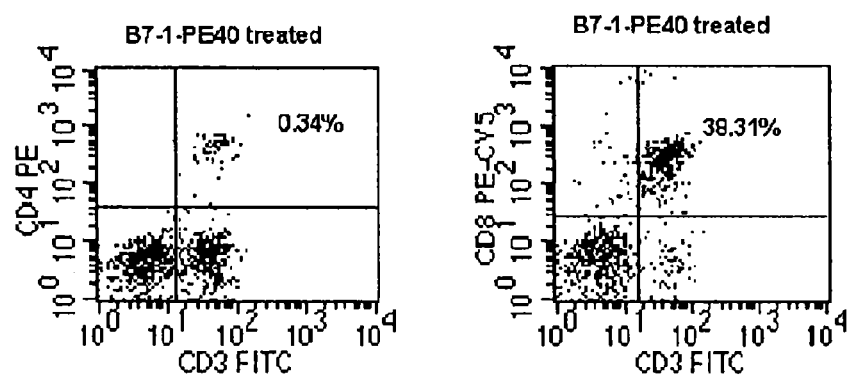
Figure 27C:
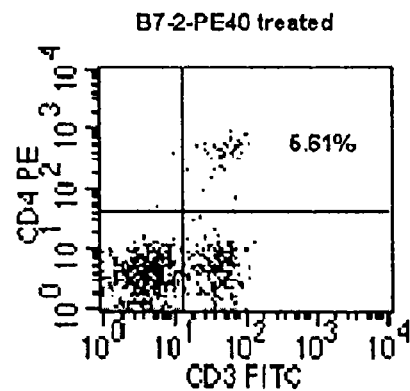
Figure 27D:
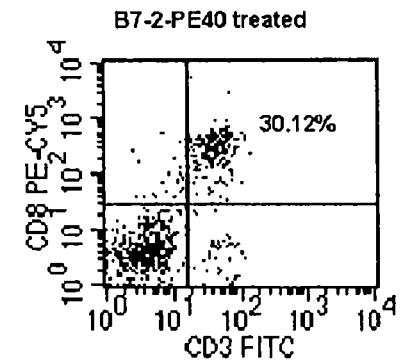
Figure 27E:
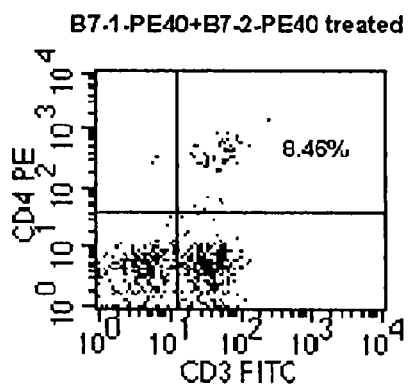
Figure 27F:
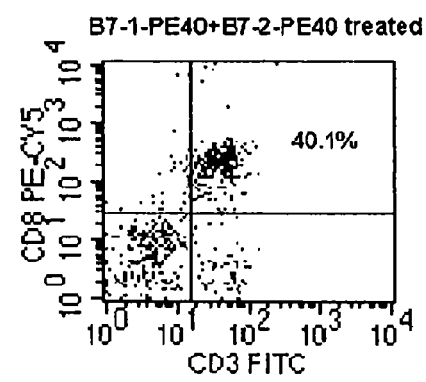
Figure 27G:
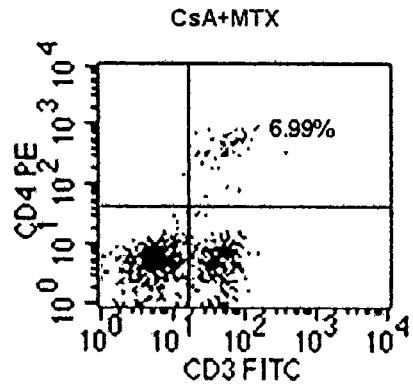
Figure 27H:
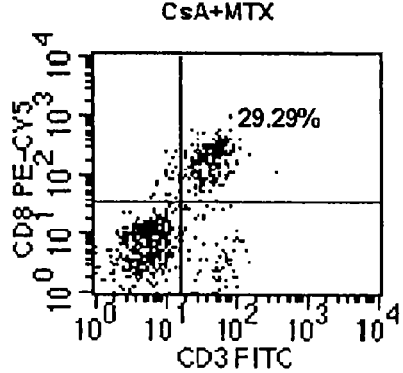
Figure 27I:
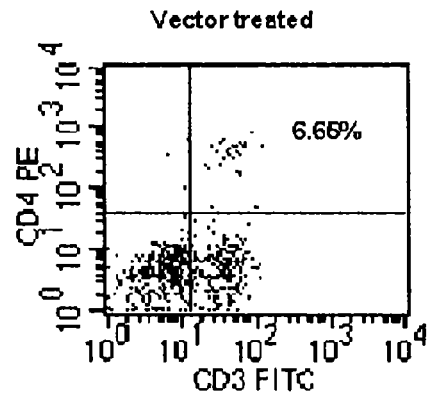
Figure 27J:
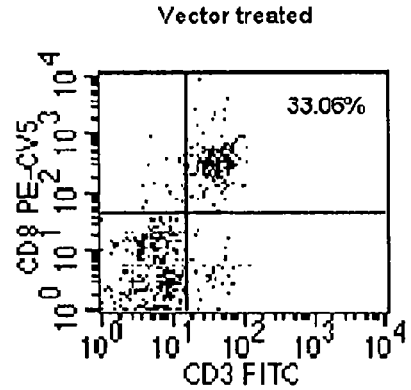
Figure 27K:
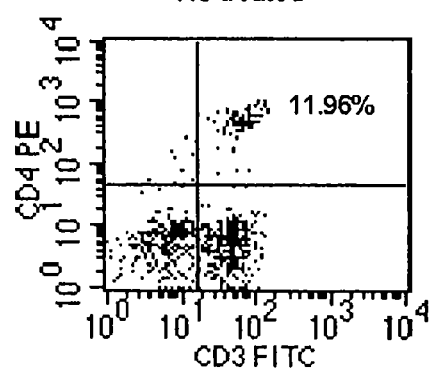
Figure 27L:
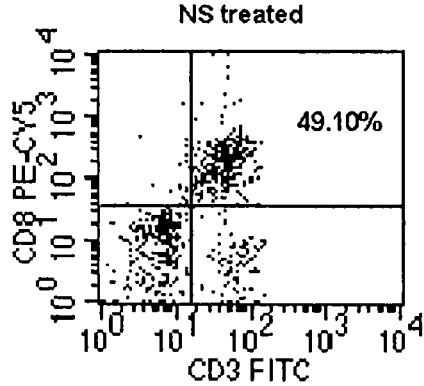
Figure 27M:
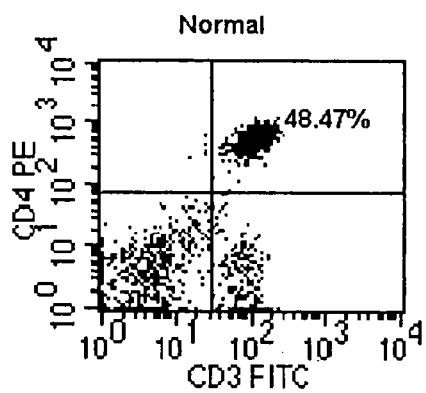
Figure 27N:
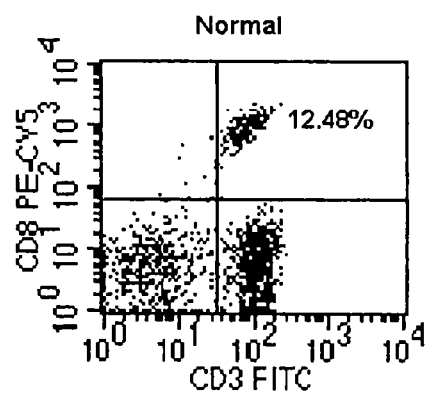

FIGS. 27A through N. Representative photos of flow cytometric analysis of $CD3^+CD4^+T/CD3^+CD8^+T$ ratios of peripheral blood in all groups.

Figure 28:
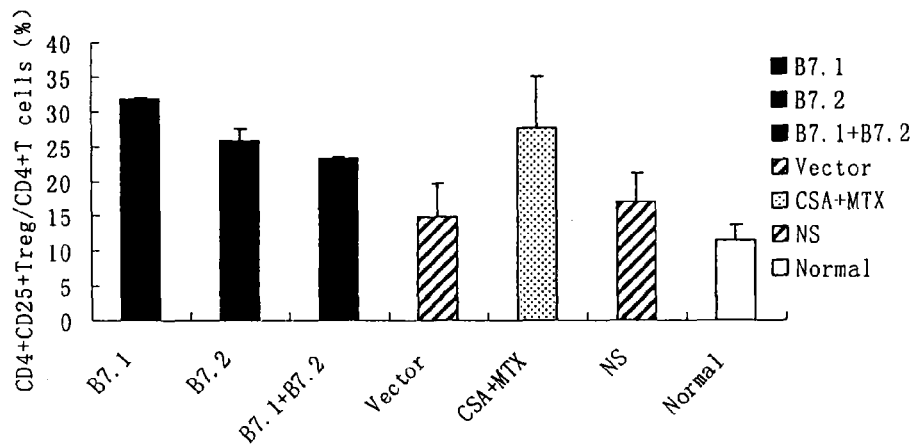
Figure 29A:
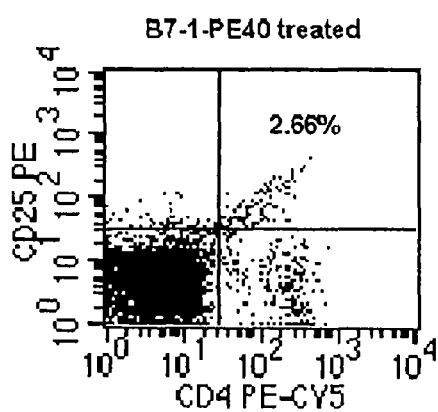
Figure 29B:
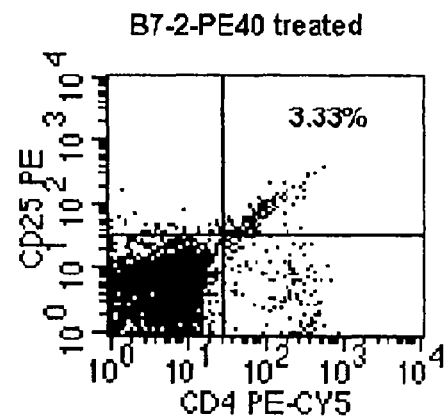
Figure 29C:
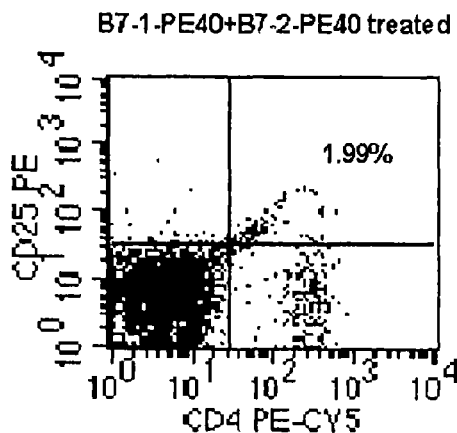
Figure 29D:
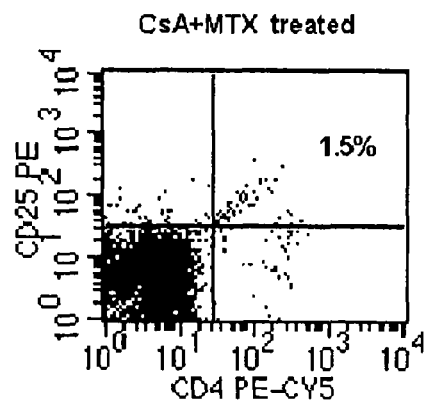
Figure 29E:
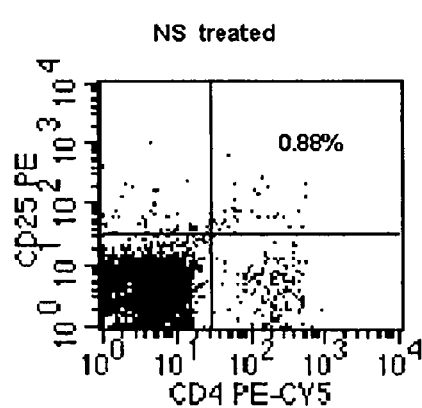
Figure 29F:
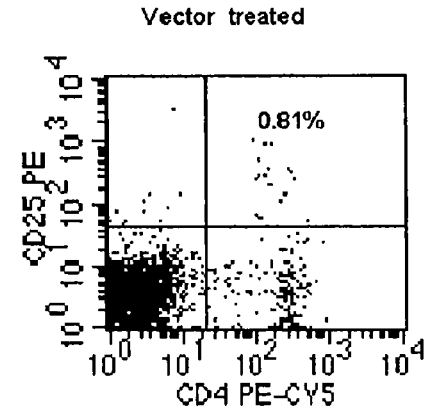
Figure 29G:
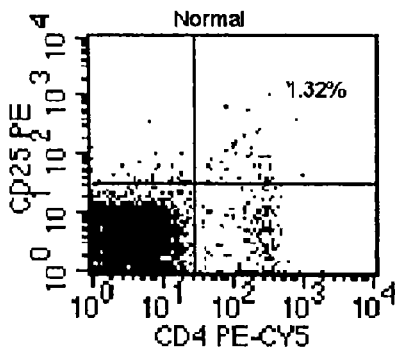

FIG. 28. The effect of DNA vaccine on $CD4^+CD25^+Treg/CD4^+T$ ratios of peripheral blood in all groups.

FIGS. 29A through G. Representative photos of flow cytometric analysis of $CD4^+CD25^+Treg$ ratios of peripheral blood in all groups.

Figure 30:
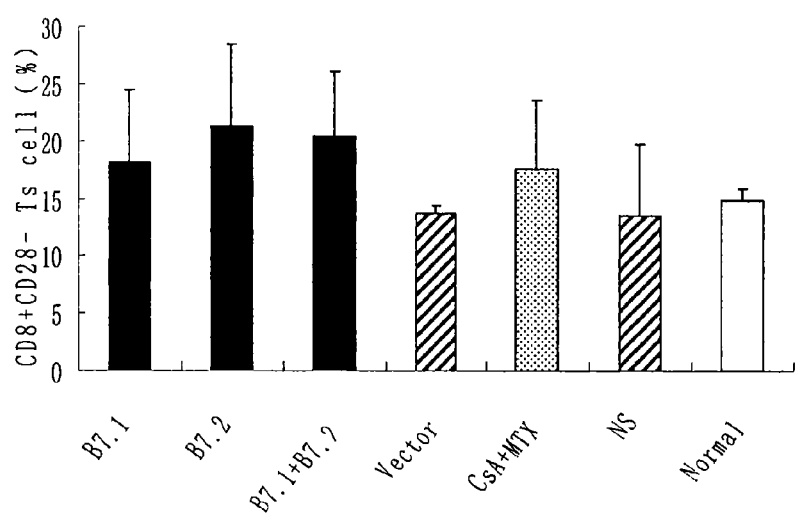
Figure 31A:
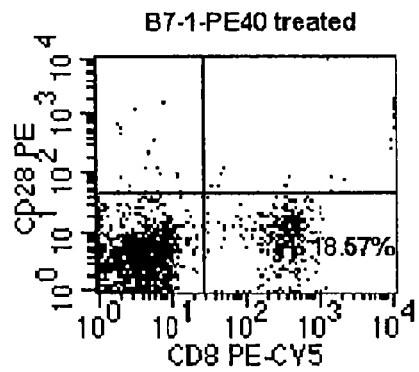
Figure 31B:
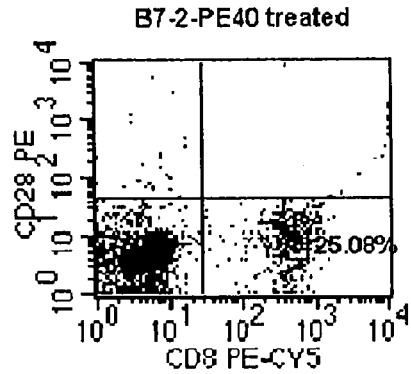
Figure 31C:
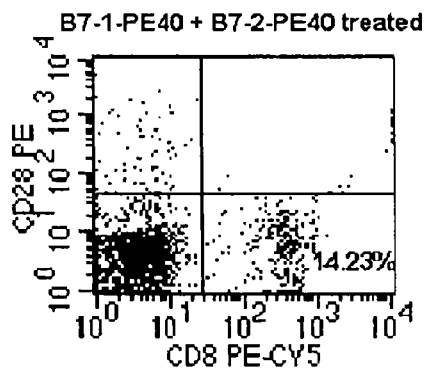
Figure 31D:
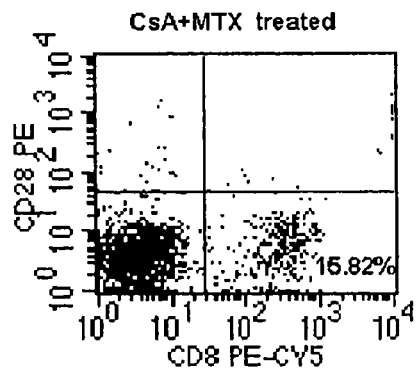
Figure 31E:
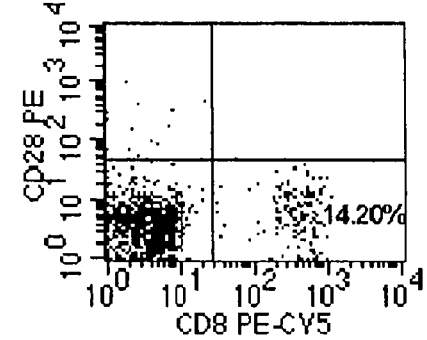
Figure 31F:
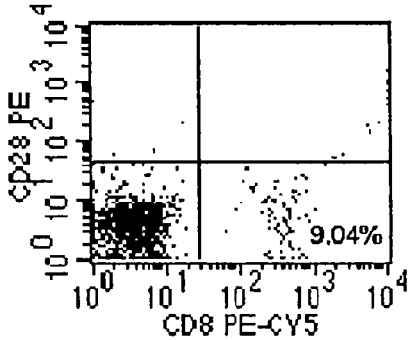
Figure 31G:
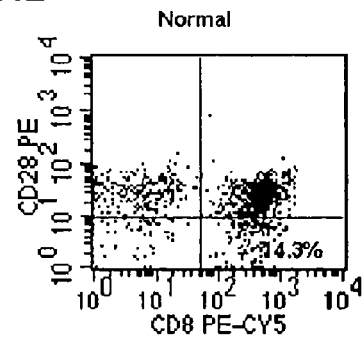

FIG. 30. The effect of DNA vaccine on $CD8^+CD28^-Ts$ ratios of peripheral blood in all groups.

FIGS. 31A through G. Representative photos of flow cytometric analysis of $CD8^+CD28^-Ts$ ratios of peripheral blood in all groups.

DETAILED DESCRIPTION OF THE INVENTION

The embodiment of the invention is described in detail below using examples. A person skilled in the art should note that the following examples are only used to explain the invention and should not be regarded as the limits of the invention scope. For the examples in which the specific techniques or conditions are not noted, the techniques and conditions are based on those described in the literature in this field (e.g., J. Sambrook et al., [translated by Peitang Huang et al.], Laboratory Manual of Molecular Cloning, Third Edition, Science Press) or the product manual. If the manufacturers of reagents or instruments are not noted, the reagents or instruments are all conventional products that can be purchased commercially.

Example 1

Construction of Eukaryotic Expression Vector pcDNA3.1/B7-1-PE40KDEL

1. Materials and Methods
1.1 Plasmids, Cells, and Main Reagents

The prokaryotic expression vector pGEMT-B7-1-PE40KDEL (2003.3.3) was constructed by our group, the strain contains said vector named as *Escherichia coli* DHA5α-pGEMT-B7-PE40KDEL, was deposited at Jun. 27, 2011 in the deposition number CGMCC NO. 4987 at China General Microbiological Culture Collection Center, No 1 Building, No. 3, Beichen west Road, Chaoyang district Beijing, China). The expression vector pcDNA3.1/Zeo(+) was stored in our department. Zeocin™, TRIzol, and Lipofectamine™2000 were purchased from Invitrogen Corp. DMEM/F12 medium was purchased from Gibco Inc. The Jurkat and Raji cell lines were stored in our department. The CHO-K1-RPE.40 cell line was established by J M Moehring and T J Moehring and was kindly provided by Dr. Sucic Joseph. The rabbit polyclonal anti-Pseudomonas exotoxin A antibody was purchased from Sigma Inc. CD80 monoclonal antibody was purchased from R&D Inc. PVDF membrane (polyvinylidene fluoride) and Amicon Ultra-4 were purchased from Millipore Inc. Super enhanced chemiluminescence detection reagents was purchased from Pierce Inc. MTS (CellTiter 96 AQueous One Solution Cell Proliferation Assay), and the PureYield™ plasmid midiprep system were purchased from Promega Co. Ltd. A reverse transcription kit, SYBR® Premix Ex Taq™, Kpn I, Xba I, and T4 ligase were purchased from TaKaRa Bio. Inc. TMB (3,3',5,5'-Tetramethylbenzidine) chromogenic substrate solution and 2×Pfu PCR MasterMix were purchased from Tiangen Biotech (Beijing) Co., Ltd. The QIAquick gel extraction kit was purchased from QIAGEN Inc.

1.2 Main Instruments

The main instruments used included a 9700 PCR instrument (PerkinElmer), Du® 640 ultraviolet detector (Beckman), Mini II protein electrophoresis instrument and protein semi-dry electrotransfer instrument (Bio-Rad), Gel-Pro3.1 gel imaging system (Media Cybernetics), 550 automatic microplate reader, and real-time quantitative PCR instrument (Stratagene, Mx3005P).

1.3 Construction of Eukaryotic Expression Vector pcDNA3.1/B7-1-PE40KDEL

The upstream primer (P1) containing the signal peptide sequence and Kpn I restriction sites and the downstream primer (P2) containing the Xba I restriction sites were designed. The signal peptide sequence was based on the sequence of the pSecTag2-B vector of Invitrogen Inc., Murine Ig k-chain V-J2-C signal peptide, which can be secreted in a large amount into the extracellular space. The sequences of the primers were as follows:

Upstream Primer P1:
5'GGTACCT*ATG* GAGACAGACACACTCCTGC-TATGGGTACTGCTGCTCTGGGTTCCAGGTT CCACTGGTGACGTTATCCACGTGACCAAGGAAGTG 3' (SEQ ID NO: 4, in which the underlined section is the Kpn I restriction site, the framed section is the start codon, and the italicized section is the signal peptide coding sequence).

Downstream Primer P2:
P2: 5'TCTAGATTACAGCTCGTCCTTCGGCGG 3' (SEQ ID NO: 5, in which the underlined section is the Xba I restriction site)

Because the P1 sequence with the added signal peptide sequence was too long, the spliced overlap extension (SOE)-PCR method was used to split P1 into two primers for overlapping amplification.

P1-A:
(SEQ ID NO: 6)
5' CTGCTCTGGGTTCCAGGTTCCACTGGTGACGTTATCCACGTGACCAAGGAAGTG 3'

P1-B:
(SEQ ID NO: 7)
5' GGTACCTATGGAGACAGACACACTCCTGCTATGGGTACTGCTGCTCTGGGTTCCA 3'

A prokaryotic expression vector, GEMT-B7-1-PE40KDEL plasmid, was used as the template, and high-fidelity Pfu DNA polymerase was used for PCR amplification. The reaction system was as follows:

| | |
|---|---|
| 2x Pfu PCR Master Mix | 12.5 μl |
| P1 (20 μM) | 0.5 μl |
| P2 (20 μM) | 0.5 μl |
| pGEMT-B7-1-PE40KDEL (1:50) | 3 μl |
| ddH$_2$O | 8.5 μl |
| Total Volume | 25 μl |

The PCR reaction conditions were as follows: pre-denaturing at 96° C. for 5 min, denaturing at 96° C. for 1 min, annealing at 63° C. for 1 min, and extension at 72° C. for 2 min for 30 cycles, followed by extension at 72° C. for 10 min. The products were resolved using 1% agarose gel electrophoresis.

The PCR products were recovered. The recovered PCR products and pcDNA3.1/Zeo(+) vector were double-digested with Kpn I+Xba I, and the digested products were recovered after electrophoresis. The digestion system was as follows:

| | |
|---|---|
| 10x Buffer M | 2 μl |
| Xba I | 1 μl |
| Kpn I | 1 μl |
| 0.1% BSA | 2 μl |
| Recovered PCR Products and pcDNA3.1/Zeo(+) Vector | 14 μl |
| Total Volume | 20 μl |

The mixture was placed in a water bath at 37° C. for 3 h.
The digested products were recovered according to the following steps:
1) The target band from the agarose gel was cut off with a clean blade and placed in a 1.5 ml EP tube.
2) The gel was weighed, and a corresponding volume of Buffer QG was added at the ratio of 100 mg gel: 300 μl Buffer QG.
3) The gel was incubated in a water bath at 50° C. for 10 min until it was completely dissolved, and the tube was then inverted upside down every 2-3 minutes to mix thoroughly.
4) One volume of isopropanol was added and mixed thoroughly.
5) The sample was loaded into a QIAquick column and centrifuged for 1 min. After the waste liquid was discarded, 0.5 ml Buffer QG was added, and the sample was centrifuged for an additional minute.
6) After the waste liquid was discarded and 0.75 ml of Buffer PE was added, the column rested for 2-5 min and was centrifuged for 1 min.

7) After the waste liquid was discarded, the column was centrifuged for 1 min and then placed into a clean 1.5 ml EP tube.
8) Thirty microliters of injection-grade $H_2O$ was added to the center of the column membrane, and after resting for 1 min, the tube was centrifuged for 1 min. The eluent was then collected.
9) The double-digested PCR products and pcDNA3.1/Zeo (+) vector were ligated. The ligation reaction was as assembled follows:

| | |
|---|---|
| 2x T4 Ligase Buffer | 5 μl |
| T4 Ligase | 1 μl |
| Double-digested PCR Products | 3 μl |
| Double-digested pcDNA3.1/Zeo(+) Vector | 1 μl |
| Total Volume | 10 μl |

The tube filled with ligation reaction was placed in 4° C. ice water to overnight.

The following method was used to transfect the ligation product into DH5a competent bacteria:

1) Five microliters of ligation product and 20 μl of reagent A were diluted with sterile water to 100 μl; the reaction was then placed on ice for later use.

2) DH5a competent bacteria were thawed on ice (5 min), and the diluted plasmid from above was then added.

3) The mixture was placed on ice for 20 min and then rested at room temperature for 10 min. The bacteria were plated onto culture plates and incubated at 37° C. overnight.

Ampicillin-resistant bacterial clones were selected to extract plasmids, which were then screened by double-digestion with restriction enzymes (the same conditions as described above). The positive clones were sent to TaKaRa Bio., Inc. for sequencing.

The bacterial clones with the correct sequence were cryopreserved, cultured and deposited. the strain deposited in the name of *Escherichia coli* DHA5α-pcDNA3.1/B7-1-PE40KDEL at Jun. 27, 2011 in China General Microbiological Culture Collection Center (No 1 Building, No. 3, Beichen west Road, Chaoyang district Beijing, China), the deposition number is CGMCC NO. 4986). The PureYield™ plasmid extraction kit was used to extract and purify large amounts of plasmids. The purified plasmids were dissolved in saline with an $OD_{260/280}$ ratio of 1.8-2.0 and a concentration of >0.5 μg/μl.

1.4 Transient Expression of Recombinant Plasmid pcDNA3.1/B7-1-PE40KDEL in CHO-K1-RPE.40 cells After $0.5 \times 10^5$-$2 \times 10^5$ CHO-K1-RPE.40 cells were seeded into 6-well plates (2 ml of medium: DMEM/F12, 7.5% FBS, 1× non-essential amino acids), the Liposome transfection method was adopted: 4 μl of plasmid and 10 μl of Lipofectamine™2000 were each diluted with 250 μl of OPTI-MEM I medium and were then mixed and incubated for 20 min. The mixture was slowly added to the 6-well plates, which were then incubated at 37° C., 5% $CO_2$ for 6 h. Then, the medium was replaced with complete DMEM medium. After 48 h, the cells and supernatant were collected and screened using RT-PCR and Western blot analysis.

1.5 RT-PCR Analysis of B7-1-PE40KDEL mRNA in Transfected Cells

Forty-eight hours after transfection, CHO-K1-RPE.40 cells in growth phase were rinsed twice with PBS. Total RNA was extracted in accordance with the instructions of the TRIzol kit and was then reverse-transcribed into cDNA for PCR amplification using the aforementioned P1 and P2 primers. β-actin was used as the reference control.

The reverse transcription reaction was assembled as follows:

| | |
|---|---|
| $MgCl_2$ | 2 μl |
| 10x RNA PCR Buffer | 1 μl |
| dNTP Mixture | 1 μl |
| RNase Inhibitor | 0.25 μl |
| AMV | 0.5 μl |
| Oligo dT | 0.5 μl |
| RNA | 4.75 μl |
| Total Volume | 10 μl |

The reaction conditions were 42° C. for 30 min, 99° C. for 5 min, then 5° C. for 5 min.

The PCR reaction system was as follows:

| | |
|---|---|
| $MgCl_2$ | 3 μl |
| 10x LA Buffer | 4 μl |
| $ddH_2O$ | 31.75 μl |
| LA Taq | 0.25 μl |
| P1 (20 μm) | 0.5 μl |
| P2 (20 μm) | 0.5 μl |
| First-Strand cDNA | 10 μl |
| Total Volume | 50 μl |

The reaction conditions were as follows: pre-denaturing at 96° C. for 5 min, denaturing at 96° C. for 1 min, annealing at 55° C. for 1 min, and extension at 72° C. for 3 min for 30 cycles, followed by extension at 72° C. for 10 min. The PCR products were identified with 1% agarose gel electrophoresis.

The sequences of the β-actin primers were as follows:
Upstream primer P1: 5'CTG TGG CAT CCA CGAAAC TA 3' (SEQ ID NO: 8)
Downstream primer P2: 5'ACA TCT GCT GGA AGG TGG AC 3' (SEQ ID NO: 9)

1.6 Western Blot Analysis of B7-1-PE40KDEL Protein Expression in Transfected Cells 1) Protein electrophoresis: Forty-eight hours after transfection, the supernatant of the CHO-K1-RPE.40 cell culture was collected and concentrated. Subsequently, 15 μl of sample and 15 μl of 2×SDS loading buffer were combined and boiled for 5 min for sodium dodecyl sulfate-polyacrylamide gel electrophoresis (SDS-PAGE). Protein electrophoresis was conducted at 80 V until protein bands had migrated out of the stacking gel, followed by electrophoresis at 150 V until the protein bands had reached the bottom of the separating gel, at which point the power was disconnected. The formulation of the protein electrophoresis was as follows:

| | 10% Separating gel (5 ml) | 5% Stacking gel (2 ml) |
|---|---|---|
| $ddH_2O$ | 1.90 ml | 1.40 ml |
| 30% Acrylamide | 1.70 ml | 0.33 ml |
| 1.5M Tris-HCl (pH 8.8) | 1.30 ml | — |
| 1.0M Tris-HCl (pH 6.8) | — | 0.25 ml |
| 10% SDS | 0.05 ml | 0.02 ml |
| 10% Ammonium persulfate | 0.05 ml | 0.02 ml |
| TEMED | 0.002 ml | 0.002 ml |

2) Membrane transfer: proteins were electro-transferred to a polyvinylidene difluoride (PVDF) membrane. Immobilon-P selected as the PVDF membrane, which was soaked in methanol for 15 s, then in water for 2 min, and then in electro-transfer buffer for 20 min. Meanwhile, the filter paper and gel were soaked in electro-transfer buffer for 15 min. The transfer system was set up as +(white)/three layers of filter paper/membrane/gel/three layers of filter paper/black. The transfer was performed at 60 mA for 40 min.

3) The membrane was blocked at room temperature for 2 h.

4) Primary antibody, rabbit anti-PEA antiserum, or CD80 monoclonal antibody that was appropriately diluted with the blocking solution was added, and the membrane was incubated at 4° C. overnight.

5) The membrane was washed with TBST 3 times for 5 min each time.

6) HRP-anti-rabbit or HRP-anti-goat IgG secondary antibody diluted with the blocking solution was added, and the membrane was incubated at room temperature for 1 h.

7) The membrane was washed with TBST 3 times for 10 min each time.

8) The ECL method was used to develop images of the gels.

1.7 Stable Transfection of CHO-K1-RPE.40 Cells with Recombinant Plasmid pcDNA3.1/B7-1-PE40KDEL Liposome transfection was performed with the same procedures outlined in section 1.4. Twenty-four hours after transfection, the transfected cells were diluted at a 1:20 ratio, and Zeocin™ was added to a concentration of 800 g/ml. The medium was replaced every 4 days, and cells were seeded into 24-well plates as the Zeo (+) clones gradually increased in size. Once the cells reached confluence, they were seeded into 6-well plates for continual culturing in multiple plates. Cells were identified by the real-time quantitative RT-PCR method, and positive cell clones were cryopreserved and stored for later use.

1.8 Enzyme-Linked Immunosorbent Assay (ELISA) Analysis of B7-1-PE40KDEL Protein Expression in Transfected Cells 1) Forty-eight hours after transfection, the supernatant of the stably transfected cell culture was collected and concentrated.

2) Ten microliters of the concentrate was diluted at a 1:10 ratio and was then added to 96-well plates overnight. The volume in each well was 1001, and three parallel wells were set up for each sample.

3) The samples were blocked with blocking solution for 1 h.

4) Anti-PEA polyclonal antibody was added and incubated at 37° C. for 1 h.

5) The plates were rinsed with PBST 3 times.

6) HRP-anti-rabbit IgG was added and incubated at 37° C. for 1 h.

7) The plates were rinsed with PBST 3 times.

8) Chromogenic TMB solution was added, and 15 min later, the reaction was terminated with 2 mol/L $H_2SO_4$. The absorbance values were measured at 450 nm, and the corresponding concentrations were calculated.

9) The untransfected cells were used as a blank control, and PEA was used as the standard to graph the standard curve (Kirman J R, Seder R A. DNA vaccination: the answer to stable, protective T-cell memory? Curr Opin Immunol, 2003, 15: 471-476).

1.9 Selective Cytotoxicity Analysis of Eukaryotic Expressed B7-1-PE40KDEL

Human lymphoma cell line Jurkat cells with a high expression level of CD28 and positive CHO-K1-RPE.40 cells stably transfected with pcDNA3.1/B7-1-PE40KDEL were co-cultured in 96-well plates at a concentration of $1\times10^5$/ml at 37° C. and 5% $CO_2$ for 48 h. Then, 20 μl of MTS was added; 1 h later, the absorbance values at 490 nm were measured, and cytotoxic activity was calculated. The human Burkitt's lymphoma cell line Raji with a lower expression level of CD28 was used as a negative control. The cell death rate was calculated as follows:

Cell death rate=(1−the number of surviving cells in the well of co-cultured stably transfected CHO-K1-RPE.40 cells and target cells/the number of surviving cells in the well of co-cultured untransfected CHO-K1-RPE.40 cells and target cells)× 100%.

Figure 2:
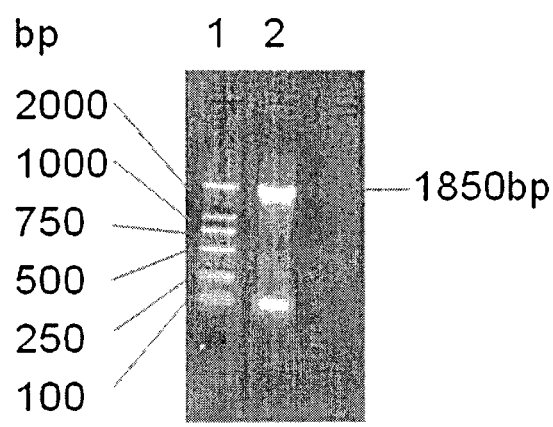
Figure 3:
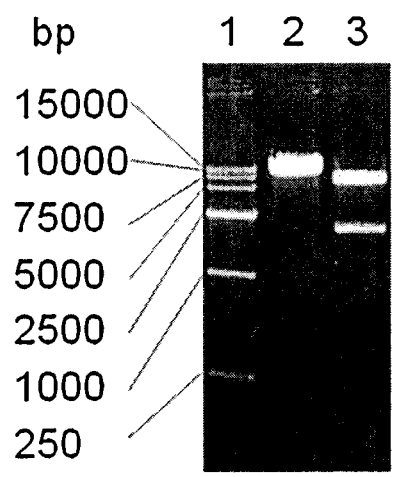

2. Results 2.1 Construction of Eukaryotic Expression Vector pcDNA3.1/B7-1-PE40KDEL To express B7-1-PE40KDEL fusion gene in eukaryotic cells, a eukaryotic expression vector pcDNA3.1/B7-1-PE40KDEL which contains B7-1-PE40KDEL and the Zeo (+) gene, was constructed as shown in FIG. 1. The designed PCR primers were used to amplify human B7-1-PE40KDEL, which was analyzed by agarose gel electrophoresis. The expected specific band of 1,850 bp was observed (FIG. 2). The recovered double-digested products were cloned into the Kpn I and Xba I restriction sites of the eukaryotic expression vector pcDNA3.1/Zeo(+) to construct the recombinant plasmid pcDNA3.1/B7-1-PE40KDEL, which was then extracted, electrophoresed (FIG. 3), and screened by sequencing (FIG. 4. The sequence is shown in Appendix 1) to obtain positive clones. The sequencing results revealed no point mutations or frameshift mutations in the sequence following the signal peptide sequence and were consistent with the sequence of the prokaryotic expression plasmid pRSETA-B7-1-PE40KDEL. The comparison results of the primary and secondary protein structures between B7-1-PE40KDEL, human B7-1, and PE40 are shown in Table 1.

TABLE 1

Comparison of the primary and secondary protein structures between B7-1-PE40KDEL fusion protein, B7-1, and PE40.

| | B7-1-PE40 KDEL | |
|---|---|---|
| Structure | Primary structure | Secondary structure |
| B7-1-208 (1-208aa) | 25aa Leucine→Proline | No change |
| | 156aa Histidine→Arginine | |
| Link-19 (209-227aa) | | |
| PE40-360 (228-587aa) | 247aa Phenylalanine→Serine | No change |
| | 397aa Valine→Isoleucine | No change |

2.2 Expression Analysis of B7-1-PE40KDEL Exotoxin Fusion Gene from Eukaryotic Cells The eukaryotic expression vector pcDNA3.1/B7-1-PE40KDEL with the correct sequence was transiently transfected into CHO-K1-RP E.40 cells, and the following methods were used to detect the expression of B7-1-PE40KDEL fusion protein: first, RT-PCR was used to detect the expression of B7-1-PE40KDEL mRNA in the transfected cells. A specific band of 1,850 bp was present in CHO-K1-RPE.40 cells transfected with pcDNA3.1/B7-1-PE40KDEL, whereas the specific band was not observed in CHO-K1-RPE.40 cells transfected with an empty vector. β-actin PCR products were used as an internal reference (FIG. 4). Western blot analysis was then conducted to detect the antigenicity and secretion expression of the B7-1-PE40KDEL fusion protein in the cell culture supernatant. The results revealed a positive band of 62-83 kDa using either a rabbit anti-PEA antiserum or a CD80 monoclonal antibody, whereas no band was observed from cells transfected with an empty vector (FIG. 5).

2.3 Screening of Stably Transfected Cells and Expression Analysis of B7-1-PE40KDEL Fusion Protein Real-time semi-quantitative analysis of the screened out 40 clones indicated that 16 clones were positive. Those positive clones were then cultured and cryopreserved in batch (FIG. 6). To detect the amount of secretion expression of B7-1-PE40KDEL in stably transfected cells, the cell culture supernatants from a number of positive clones were sampled to graph the standard curve of protein concentration using ELISA and the known concentrations PEA as standards (Table 2, FIG. 7). The OD value of each supernatant from these samples was compared to the standard curve to obtain the secreted amount in each stably transfected clone. The results are presented in Table 3. The results indicated that 24 h post-transfection, approximately 287 pg/ml of PEA protein was expressed in $1 \times 10^6$ stably transfected cells.

TABLE 2

ELISA detection values of different concentrations PEA standard substance

| PEA Concentration (pg/ml) | OD Value |
|---|---|
| 0 | 0.105 |
| 78.125 | 0.177 |
| 156.25 | 0.232 |
| 312.5 | 0.47 |
| 625 | 0.627 |
| 1250 | 1.143 |
| 2500 | 1.772 |
| 5000 | 2.477 |

$OD_{450}$ was used as the ordinate and PEA concentrations as the abscissa to graph the standard curve using Curve Expert 1.3 software. The standard curve of the polynomial fitting equation (FIG. 7) was used to calculate the PEA concentrations from the culture supernatant of stably transfected cell strains.

TABLE 3

The expression levels of B7-1-PE40KDEL fusion proteins in different positive clones

| Clone No. | OD450 Value | PEA Concentrations (pg/ml) |
|---|---|---|
| Clone 1* | 0.352 | 268.26 |
| Clone 2* | 0.317 | 230.3 |
| Clone 4 | 0.385 | 303.98 |
| Clone 32 | 0.425 | 347.28 |

2.4 Selective Cytotoxicity of the Eukaryotic Expressed B7-1-PE40KDEL

The human lymphoma cell line Jurkat with a high expression level of CD28 was used to detect the selective cytotoxic activity of the eukaryotic expressed B7-1-PE40KDEL. The human Burkitt's lymphoma cell line Raji with a low expression level of CD28 was used as a negative control. The MTT results indicated that after 48 h of co-incubation of stably transfected cells and Jurkat cells, the OD value was 0.782, whereas the OD values were 1.466 for untransfected cells, 1.29 for Jurkat cells alone, 1.296 for the co-incubation of stably transfected cells and Raji cells, and 1.564 for untransfected cells alone. According to the equation, the The percentage of cell killing of Jurkat cells and Raji cells by the stably transfected cells were 92.87% and 15%, respectively, these result confirmed that the eukaryotic expressed B7-1-PE40KDEL have a good selective inhibitory effect on CD28-positive cells in vitro. (FIG. 8).

Example 2

The Protection Against aGVHD by B7-1-PE40KDEL DNA Vaccine (1)

1. Materials and Methods 1.1 Plasmids, Cells, and Main Reagents

The eukaryotic expression vector pcDNA3.1/B7-1-PE40KDEL was constructed by our group. This eukaryotic expression vector was previously constructed and stored by Dr. Hong Xue. The rabbit polyclonal anti-Pseudomonas exotoxin A antibody was purchased from Sigma Inc. FITC-anti-mouse CD3, PE-anti-mouse CD28, and Pharmlyse™ were purchased from BD Inc. SYBR® Premix Ex Taq™ (perfect real-time) was purchased from TaKaRa Bio. Inc. MTX for injection was purchased from Jiangsu Hengrui Medicine Co., Ltd., and cyclosporin A was purchased from Novartis Pharma Schweiz AG. Mouse lymphocyte separation solution was purchased from Tianjin Hao Yang Biological Products Co. Ltd.

The donor male mice C57BL/6 ($H2^b$) and The recipient female mice Balb/c ($H2^d$) housed in specific pathogen-free conditions weighed 16-18 g and 18-22 g at the beginning of the experiments. All experimental animals were provided by the Animal Center of the Academy of Military Medical Sciences, and the breeding conditions were at the specific pathogen-free (SPF) level. The Department of Pathology at the Affiliated Hospital of the Academy of Military Medical Sciences assisted in the preparation and observation of pathological samples. Flow cytometric analysis was conducted by the Institute of Radiation Medicine of the Academy of Military Medical Sciences. The real-time quantitative PCR analysis was conducted by the blood center of the Affiliated Hospital of the Academy of Military Medical Sciences.

1.2 Main Instruments

A WJ2002 in vivo gene transfer instrument (Scientz Biotechnology Co. Ltd.) and a 550 automatic microplate reader (Bio-Rad Laboratories, Inc.) were used in our study.

1.3 Establishment of an aGVHD Mouse Model

The recipient mice were provided with drinking water that contained gentamicin ($32 \times 10^4$ U/L) and erythromycin (250 mg/L) one week prior to the transplantation to prevent infection and were fed in a sterile laminar airflow cabinet. $^{60}$Co total body irradiation (TBI) (8.0 Gy, dose rate is 1.8 Gy/min) was administered 4 h prior to transplantation.

The preparation of donor bone marrow cells and spleen cells was as follows: C57BL/6 donor mice were sacrificed by cervical dislocation and then soaked in 75% ethanol for a few minutes. The femur was sterilely obtained with surgical scissors, and RPMI-1640 culture medium was used to flush out the bone marrow from the bone marrow cavity, which was then sifted through a 200-mesh cell sieve. Next, 0.83% ammonium chloride solution was used to lyse the erythrocytes, followed by two washes with RPMI-1640 culture medium (1000 rpm, 10 min). This produced a single-cell suspension of bone marrow cells. The cell concentration was then adjusted to $1 \times 10^8$/ml. In addition, the spleens were removed aseptically and then ground on a 200-mesh cell sieve. After the cells were collected by centrifugation, 0.83% $NH_4Cl$ solution was used to lyse the erythrocytes, followed by two washes with RPMI-1640 culture medium (1000 rpm, 10 min). The resulting single-cell suspension of spleen cells was then adjusted to a cell concentration of $1 \times 10^8$/ml.

The prepared spleen cells and bone marrow cells were infused via tail vein injections into the recipient mice of all groups. The numbers of infused cells were $2 \times 10^7$ spleen cells/mouse and $1 \times 10$ bone marrow cells/mouse. The establishment of a stable aGVHD mouse model was confirmed with physical signs, the assessment of hematopoietic reconstruction, pathological analysis, and chimerism analysis after transplantation.

1.4 Protection Protocols Against aGVHD by B7-1-PE40KDEL DNA Vaccine in aGVHD Mice Sixty aGVHD mice were randomly divided into six groups with 10 mice in each group: (1) B7-1-PE40KDEL DNA vaccine group; (2) B7-2-PE40KDEL DNA vaccine group; (3) B7-1-PE40KDEL+B7-2-PE40KDEL DNA vaccine group; (4) empty vector group; (5) CsA+MTX positive control group; and (6) untreated aGVHD group. Both the empty vector and DNA vaccine vector were dissolved in normal saline. There was no RNA contamination of the plasmid vector. Endotoxin was removed. Supercoiled DNA accounted for 70%-80% of the DNA. The $OD_{260}/OD_{280}$ ratios ranged from 1.8-2.0. The concentration was not less than 0.5 μg/μl. The preliminary experiment indicated that when a 75 g of B7-1-PE40KDEL DNA vaccine was infused, the protection against aGVHD was good with few side effects. Immediately after transplantation, 75 μg of empty vector or DNA vaccine vector was injected into mice quadriceps, and electrical impulse-mediated stimulation was given at the injection site to efficiently deliver the genes into the body. The pulse parameters were as follows: voltage, 200 V/cm; pulse width, 10 ms; the number of pulses, 6; frequency, 1 Hz (Mir L M, Bureau M F, Gehl J, et al. High-efficiency gene transfer into skeletal muscle mediated by electric pulses. Proc. Natl. Acad. Sci. USA, 1999, 96: 4262-4267). The "gold standard" regimen CsA+MTX that has been commonly used in clinical practice, was adopted as the control drugs. CsA was administered via intraperitoneal injection once per day at a dose of 1.5 mg/kg·d. MTX was administered via intraperitoneal injection on days 1, 3, 6, and 11 at a dose of 0.4 mg/kg·d (Xu K, Li C, Pan X, et al. Study of Relieving Graft-versus-Host Disease by Blocking CD137-CD137 Ligand Costimulatory Pathway in Vitro. Int J Hematol, 2007, 86:84-90.).

1.5 Expression of B7-1-PE40KDEL DNA Vaccine in Normal Mice

Electrical impulse-mediated intramuscular injection was used to inject 75 μg of purified B7-1-PE40KDEL DNA vaccine into the quadriceps of normal Balb/C mice, followed by electrical stimulation (200 V/cm, 10 ms, 1 Hz, 6 pulses). On days 1, 7, 14, 21, 28, and 35 after injection, the eyeballs were removed to collect blood, which was then treated with heparin. A TRIzol kit was used to extract RNA, and RT-PCR was used to qualitatively detect B7-1-PE40KDEL mRNA expression. Real-time quantitative PCR was further used to compare the blood expression levels of PE40 mRNA. β-actin was used as an internal reference.

RNA extraction was performed as follows: mouse lymphocyte-separating solution was used to isolate white blood cells from the peripheral blood of mice (approximately 1 ml), which were washed twice with PBS before 1 ml of TRIzol was added. The isolated cells rested at room temperature for 5 min, and 200 μl of chloroform was then added and mixed well by shaking. After stratification, the mixture was centrifuged at 4° C. and 12,000 g for 15 min. The upper aqueous phase was transferred to another tube, and 500 μl of isopropanol was added and mixed well. After resting at room temperature for 10 min, the mixture was centrifuged at 4° C. and 12,000 g for 10 min. The supernatant was discarded, and RNA was at the bottom of the tube, which was washed with 75% ethanol and then centrifuged at 4° C. and 8000 g for 5 min. The supernatant was then discarded. After the complete evaporation of ethanol, RNA was dissolved with an appropriate amount of DEPC-treated water and quantitatively measured with a UV spectrophotometer.

The reaction conditions of reverse transcription were as follows:

| | |
|---|---|
| $MgCl_2$ | 2 μl |
| 10x RNA PCR Buffer | 1 μl |
| dNTP | 1 μl |
| RNase Inhibitor | 0.25 μl |
| AMV | 0.5 μl |
| Oligo dT | 0.5 μl |
| RNA | 0.5 μg |
| Total volume | 10 μl |

The reaction conditions were 42° C. for 30 min, 99° C. for 5 min, and 5° C. for 5 min.

The sequences of mouse β-actin primers were:
Upstream primer P1: 5'AGG CAT CCT GAC CCT GAA GTA C 3' (SEQ ID NO: 10)
Downstream primer P2: 5'TCT TCA TGA GGTAGT CTG TCA G 3' (SEQ ID NO: 11)

The PCR reaction was assembled as follows:

| | |
|---|---|
| SYBR ® Premix Ex Taq ™ (2x) | 12.5 μl |
| $ddH_2O$ | 10.5 μl |
| P1 (20 μM) | 0.5 μl |
| P2 (20 μM) | 0.5 μl |
| cDNA | 1 μl |
| Total Volume | 25 μl |

Real-time PCR reaction:
Segment 1: pre-denaturing
Repeat: 1 cycle
95° C. for 5 min
Segment 2: PCR reaction
Repeat: 35 cycles
94° C. for 30 s
59° C. for 30 s
72° C. for 60 s
Segment 3: Dissociation.

1.6 In Vivo Activity of B7-1-PE40KDEL DNA Vaccine in Normal Mice

On days 1, 7, 14, 21, 28, and 35 after the injection of 75 μg of purified B7-1-PE40KDEL DNA vaccine, the mice eyeballs were removed, and blood was collected and treated with heparin. One microliter of both FITC-anti-mouse CD3 and PE-anti-mouse CD28 was added to 100 μl of anticoagulant blood, followed by incubation at room temperature in the dark for 30 min. Next, 2 ml of Pharmlyse™ erythrocyte lysis buffer was added, followed by incubation at room temperature in the dark for 15 min. The mixture was then centrifuged at 1500 rpm for 5 min. After the supernatant was discarded, the pellet was re-suspended with PBS followed by centrifugation at 1500 rpm for 5 min. After the supernatant was discarded, 0.5 ml of 2% paraformaldehyde-PBS was added for detection.

1.7 The Detection of Anti-PEA Antibody in Normal Mice Treated with B7-1-PE40KDEL DNA Vaccine (Chen S Y, Yang A G, Chen J D, et al. Potent Antitumor Activity of a New Class of Tumor-Specific Killer Cells. Nature, 1997, 385:78-80.)

On day 21 after the intramuscular injection of B7-1-PE40KDEL DNA vaccine, the mice eyeballs were removed, the blood was collected and centrifuged, and the serum was stored at −20° C. for later use. ELISA was performed as follows: PEA (1 mg/mL) was dissolved in coating buffer, and each well was coated with 200 ng/1001, followed by incubation at 4° C. overnight. The next day, the wells were washed 2-3 times with PBST and then blocked in bovine serum blocking solution at room temperature for 2 h. The serum sample and standard samples (100 μl/well) were incubated at 37° C. for 1 h and then washed 3 times with PBST. Next, 100 μl of HRP-anti-mouse IgG diluted at a ratio of 1:50,000 was added to each well and incubated at 37° C. for 1 h. After washing 4 times with PBST, 100 μl of TMB chromogenic solution was added to each well and incubated at 37° C. for 15 min. The reaction was terminated by adding 50 Cl of 2 M $H_2SO_4$ to each well, and the absorbance values were measured at 450 nm. The rabbit anti-PEA polyclonal antibody was used as a positive control, and the serum from mice injected with pcDNA3.1 empty vector was used as a negative control.

1.8 The Toxicity and Side Effects of B7-1-PE40KDEL DNA Vaccine

After the intramuscular injection of 75 g of B7-1-PE40KDEL DNA vaccine, the physical signs and behavior of the mice were observed. In addition, on days 7, 14, and 21, the heart, liver, spleen, lung, and kidney were taken for histopathological examination to make preliminary observations as to whether there was toxicity or side effects of B7-1-PE40KDEL DNA vaccine in mice.

1.9 The Effect of B7-1-PE40KDEL DNA Vaccine on the Physical Signs of GVHD Mice

The mice in all groups were weighed each day, and physical signs such as hair, spirit, and diarrhea were observed.

1.10 The Effect of B7-1-PE40KDEL DNA Vaccine on Hematopoietic Reconstruction in GVHD Mice After the preconditioning, 20 μl of blood was collected from the tail vein and diluted with 3801 of white cell diluent for white blood cell counts with hemacytometer at regular intervals, which was used to understand the changes in blood and hematopoietic reconstruction in mice from all groups.

1.11 The Effect of B7-1-PE40KDEL DNA Vaccine on Chimerism in GVHD Mice

Different genders of mice were used as the donor and recipient in bone marrow transplantation.

Therefore, the genomic DNA could be extracted from the peripheral blood of female recipient mice and the Y chromosome-specific gene sry primers could be designed to PCR-amplify the Y chromosome of male donor mice to detect transplant engraftment.

```
sry primer 1:
                              (SEQ ID NO: 12)
5'-TGTGGTCCCGTGGTGAGA-3';

primer 2:
                              (SEQ ID NO: 13)
5'-ATCAACAGGCTGCCA ATAAA-3'.
```

1.12 The Effect of B7-1-PE40KDEL DNA Vaccine on Histopathology in GVHD Mice

On day 21 after transplantation, the livers, spleens, small intestines, and skin of mice in all groups were removed and fixed in 10% formalin solution, followed by paraffin sectioning and HE staining to observe the pathological changes.

1.13 Statistical Analysis

SPSS 13.0 software was used for statistical analysis. The t tests were used to test the statistical significance of the differences in the mean measurement data between the two groups. A non-parametric test (the Mann-Whitney test) was used to compare ranked data between the two groups. $P<0.05$ was considered statistically significant. SPSS 13.0 software was also used to graph the Kaplan-Meier survival curve.

2. Results 2.1 The Expression of B7-1-PE40KDEL DNA Vaccine in Normal Mice

The RT-PCR results (FIG. 9) indicated that on days 1, 7, 14, 21, 28, and 35 after the injection of the B7-1-PE40KDEL DNA vaccine, B7-1-PE40KDEL mRNA was detectable. We used β-actin as an internal reference.

Real-time quantitative PCR (FIG. 10) showed that the expression of PE40KDEL mRNA was relatively higher on days 1 and 7, and then the expression level gradually declined with time to the lowest levels on days 28 and 35.

2.2 The In Vivo Activity of B7-1-PE40KDEL DNA Vaccine in Normal Mice

Because B7-1-PE40KDEL can specifically kill cells with high expression levels of CD28, flow cytometric analysis was conducted to analyze the removal of $CD28^+T$ cells from the peripheral blood of mice injected with B7-1-PE40KDEL DNA vaccine, which was indicated as geometric mean fluorescence intensity (Geo mean) (FIG. 11). The results showed that on day 7 after the intramuscular injection of B7-1-PE40KDEL DNA vaccine, the effect of $CD28^+T$ removal began to appear, and the Geo mean of blood $CD28^+T$ cells was lower than that of normal control mice. On day 21 after injection, $CD28^+T$ count declined to the lowest level. On days 28 and 35 after injection, $CD28^+T$ count gradually recovered, but the Geo mean of $CD28^+T$ cells was still lower than that of normal mice. The results suggested that with the declining expression level of B7-1-PE40KDEL, $CD3^+CD28^+T$ cells showed a trend towards recovering to a normal level (FIG. 12).

2.3 Detection of Serum Anti-PEA Antibody Levels in Mice after the Intramuscular Injection of B7-1-PE40KDEL DNA Vaccine The anti-PEA antibody level was detected using ELISA. A commercial anti-PEA antibody was used as the standard to graph the standard curve. The $OD_{450}$ was used for the abscissa, and anti-PEA antibody concentration was used for the ordinate to graph the standard curve using CurveExpert 1.3 software (FIG. 13). A quadratic fitting equation was used to calculate concentrations of serum anti-PEA antibodies (Table 4). The anti-PEA antibody level of B7-1-PE40KDEL DNA vaccine intramuscular-injection group was significantly lower than that of the positive control group ($p<0.05$), and there was no significant difference when compared to that of the negative control group (i.e., the empty-vector injection group).

TABLE 4

Serum anti-PEA antibody levels in mice on day 21 after the intramuscular injection of B7-1-PE40KDEL DNA vaccine

| Groups | Absorbance Value (450 nm) | Concentration (pg/ml) |
|---|---|---|
| pcDNA3.1/B7-1-PE40KDEL (75 μg) | 0.283 ± 0.029* | 63.824 ± 6.402* |
| pcDNA3.1 group (negative control) | 0.139 ± 0.022* | 49.814 ± 1.669* |
| Positive control | 0.564 ± 0.084 | 312.458 ± 3.842 |

*indicates the comparison with the positive control, P < 0.05

2.4 Toxicity and Side Effects of B7-1-PE40KDEL DNA Vaccine in Normal Mice

After the intramuscular injection of 75 g of B7-1-PE40KDEL DNA vaccine, the mice were observed every day, and no abnormalities in physical signs or behavior were observed. Histopathological examination of hearts, livers, spleens, lungs, and kidneys removed on days 7, 14, and 21 after the injection did not reveal any pathological changes.

2.5 Establishment of an aGVHD Mouse Model

One week after transplantation, recipient mice began to experience typical GVHD symptoms, such as changes in hair color, listlessness, loss of appetite, serious epilation in the abdomen and head, diarrhea, black stool, ulcers, and hunched posture (FIG. 14). Their average body weight progressively declined at nearly 1 g/day and reached a low point of approximately 14.77±1.66 g on day 10. Afterwards, body weight began to increase and then began to gradually decline again after day 14 through death. The total weight loss was approximately 8 g at death (FIG. 15). White blood cell counts in the peripheral blood began to drop on day 1 and were lowest (0.69±0.18×10$^9$/L) on day 3~day 4. The count began to recover on day 6 and reached a peak on day 14, then continued to drop afterwards. The white blood cell count was 1.54±0.14×10$^9$/L at death. On day 35 after transplantation, the specific Y-chromosome sry gene sequence of male donor mice could be detected in the peripheral blood of all recipient mice, as shown in FIG. 16 as the 371-bp fragment, suggesting that the transplantation was successful. Pathological examination revealed typical GVHD pathological findings as follows: ① Necrosis of the glandular epithelial cells in the intestinal mucosa was observed in small intestine tissue, and necrotic cell debris was present in the epithelial cells and glandular cavity; glandular epithelial cells were flat, glands were cystic, the number of glands was reduced, glands disappeared, and the mucosal epithelium fell off (FIG. 17-A); ② In liver tissue, focal liver cell degeneration and necrosis occurred, and lymphocyte and eosinophil infiltration was observed (FIG. 17-B). Liver cells swelled and degenerated; ③ In the spleen, we observed massive bleeding, splenic fibrosis, spleen sinus expansion and bleeding, and sparse spleen cells (FIG. 17-C); ④ Fibrous tissue hyperplasia was observed in the subdermal region, and lymphocyte infiltration occurred in the dermis (FIG. 17-D). All mice in the GVHD model group died within 24 days after radiation, with a median survival time of 22.7 days. The average survival time of the bone marrow transplantation group was more than 60 days, which can be considered long-term survival. The median survival time of the spleen cell infusion group was 9.6 days. The median survival time of radiation group alone was 12.3 days. The survival rates of the mice in all groups were depicted in a Kaplan-Meier survival curve (FIG. 18). In the summation of the typical GVHD symptoms listed above, we confirmed that a stable, acute GVHD mouse model had been established, and the success rate was nearly 100%.

2.6 The effects of B7-1-PE40KDEL and B7-2-PE40KDEL DNA vaccines on the physical signs of aGVHD mice After the treatment with B7-1-PE40KDEL DNA vaccine (called as B7-1), B7-2-PE40KDEL DNA vaccine (called as B7-2), and B7-1-PE40KDEL+B7-2-PE40KDEL DNA vaccine (called as B7-1+B7-2), the symptoms of hunched posture and epilation were significantly improved compared with the other groups. The starting time of epilation in the combination treatment group was 3-6 days later than in other groups. There was no blood in the stool and no perianal swelling. The weight loss of the mice was the smallest in B7-1-PE40KDEL DNA vaccine group, followed by CsA+MTX group, B7-1-PE40KDEL+B7-2-PE40 KDEL DNA vaccine group, and B7-2-PE40KDEL DNA vaccine group. The mice in the empty vector group and the untreated GVHD group (NS group) experienced the greatest weight loss. The changes in body weight of GVHD mice in all groups after treatment are shown in FIG. 19.

2.7 The Effect of B7-1-PE40KDEL and B7-2-PE40KDEL DNA Vaccines on Hematopoietic Reconstruction of aGVHD Mice The WBC counts in the peripheral blood of the aGVHD mice in all groups began to drop on day 1 to a low point of approximately 0.6×10$^9$/L on day 3~day 4. The WBC count began to recover on day 6, and the level of recovery was higher in B7-1-PE40KDEL DNA vaccine, B7-2-PE40KDEL DNA vaccine, B7-1-PE40KDEL+B7-2-PE40KDEL DNA vaccine, and CsA+MTX groups than in the empty vector group and the untreated group. Of all groups, the level of WBC recovery was the highest in B7-1-PE40KDEL DNA vaccine group. Subsequently, WBC counts continued to drop again to >1.0×10$^9$/L at death in all groups (FIG. 20).

2.8 The Effect of B7-1-PE40KDEL and B7-2-PE40KDEL DNA Vaccines on Histopathology of aGVHD Mice Pathological analysis was performed on small intestine tissues of the mice in all groups on day 21 after treatment (FIG. 21). The results revealed good glandular epithelial cell integrity and relatively few necrotic cells in group C (B7-1-PE40KDEL+B7-2-PE40KDEL DNA vaccine) and group E (CsA+MTX). In group F (untreated aGVHD group), there was massive necrosis of the mucous glandular epithelial cells, and the shedding of mucosal epithelium was the most serious. The pathological analysis of skin (FIG. 22) revealed serious fibrous tissue hyperplasia in the subdermal region in group D (empty vector group) and group F (untreated aGVHD group). In group A (B7-1-PE40KDEL DNA vaccine), group B (B7-2-PE40KDEL DNA vaccine), group C (B7-1-PE40KDEL+B7-2-PE40KDEL DNA vaccine), and group E (CsA+MTX), the lesions were less severe, and the degree of lymphocyte infiltration was also lower than in groups D and F. Pathological analysis of the liver (FIG. 23) revealed that in group A only, the degree of liver cells' swelling and hydropic degeneration was relatively low. In other groups, there was focal liver cell degeneration and necrosis, infiltration of lymphocytes and eosinophils, and more serious liver cell swelling and degeneration.

2.9 The Effect of B7-1-PE40KDEL and B7-2-PE40KDEL DNA Vaccines on the Survival Time of aGVHD Mice The survival time of the mice in B7-1-PE40KDEL DNA vaccine group was the longest, with a median survival time of 51 days. The median survival times of B7-2-PE40KDEL DNA vaccine and B7-1-PE40KDEL+B7-2-PE40KDEL DNA vaccine groups, empty vector group, CsA+MTX group, and the untreated group were 41, 47, 22.5, 39.7, and 21.5 days, respectively. The survival rates of the mice in all groups are depicted in a Kaplan-Meier survival curve (FIG. 24).

2.10 Chimerism Evaluation of aGVHD Mice in all Groups after Treatment with B7-1-PE40KDEL and B7-2-PE40KDEL DNA Vaccines On day 21 after transplantation, the specific Y-chromosome sry gene of the male donor mice was detectable in the peripheral blood of the recipient mice in all treatment groups (FIG. 25), suggesting that the transplantation was successful in all groups.

Example 3

The Protection Against aGVHD by B7-1-PE40KDEL DNA Vaccine (2)

1. Materials and Methods
1.1 Experimental Animals

The donor male mice C57BL/6 (H2$^b$) and The recipient female mice Balb/c (H2$^d$) housed in specific pathogen-free conditions weighed 16-18 g and 18-22 g at the beginning of the experiments. All experimental animals were provided by the Animal Center of the Academy of Military Medical Sciences, and the breeding conditions were at the specific pathogen-free (SPF) level.

1.2 Drugs and Reagents

The eukaryotic expression vector pcDNA3.1/Zeo(+)-B7-2-PE40KDEL was constructed and stored in our department. The eukaryotic expression vector was constructed and stored as described in section 1. MTX for injection was purchased from Jiangsu Hengrui Medicine Co., Ltd. Cyclosporin A was purchased from Novartis Pharma Schweiz AG. FITC-anti-mouse CD3, PE-anti-mouse CD28, PE-Cy5-anti-mouse CD8, PE-Cy5-anti-mouse CD4, PE-anti-mouse CD4, and PE-anti-mouse CD25 were all purchased from BD Inc. Fluorokine MAP mouse interferon (IFN) γ, interleukin (IL)-2, IL-4, IL-10, IL-12, tumor necrosis factor (TNF) α kits, and Luminex liquid chips for cytokine detection were provided by R&D Inc. Tumor growth factor (TGF) β and IL-2 ELISA kits were provided by R&D Inc.

1.3 Establishment of an aGVHD Mouse Model

The recipient mice were provided drinking water that contained gentamicin ($32 \times 10^4$ U/L) and erythromycin (250 mg/L) one week prior to transplantation to prevent infection and were fed in a sterile laminar airflow cabinet. $^{60}$Co total body irradiation (TBI) (8.0 Gy, dose rate is 1.8 Gy/min) was administered 4 h prior to transplantation.

The preparation of donor bone marrow cells and spleen cells was as follows: C57BL/6 donor mice were sacrificed by cervical dislocation and then soaked in 75% ethanol for a few minutes. The femur was sterilely obtained with surgical scissors, and RPMI-1640 culture medium was used to flush out the bone marrow from the bone marrow cavity, which was then sifted through a 200-mesh cell sieve. Next, 0.83% $NH_4Cl$ solution was used to lyse the erythrocytes, followed by two washes with RPMI-1640 culture medium (1000 rpm, 10 min). As a result, a single-cell suspension of bone marrow cells was obtained, and the cell concentration was then adjusted to $1 \times 10^8$/ml. In addition, the spleens were removed aseptically and ground on a 200-mesh cell sieve. After the cells were collected by centrifugation, 0.83% $NH_4Cl$ solution was used to lyse the erythrocytes, followed by two washes with RPMI-1640 culture medium (1000 rpm, 10 min). As a result, a single-cell suspension of spleen cells was obtained, and then the cell concentration was adjusted to $1 \times 10^8$/ml.

The prepared spleen cells and bone marrow cells were infused via tail vein injection into the recipient mice of all groups. The numbers of infused cells were $2 \times 10^7$ spleen cells/mouse and $1 \times 10$ bone marrow cells/mouse. The establishment of a stable aGVHD mouse model was confirmed with the detection of physical signs, hematopoietic reconstruction, transplantation, and pathological analysis.

1.4 Protection Protocols Against aGVHD by B7-1-PE40KDEL DNA Vaccines in aGVHD Mice The protection protocol of B7-PE40KDEL DNA vaccine and other treatment was as follows: drugs were administered to the mice of all groups at day 1 after transplantation. There were six groups with five mice in each group, as follows: (1) B7-1-PE40KDEL DNA vaccine group; (2) B7-2-PE40KDEL DNA vaccine group; (3) B7-1-PE40KDEL+B7-2-PE40KDEL DNA vaccine group; (4) empty vector group; (5) CsA+MTX control group; (6) the untreated aGVHD group; and (7) the normal control group. Both the empty vector and DNA vaccine vector were dissolved in normal saline. There was no RNA contamination of the plasmid vector. Endotoxin was removed. Supercoiled DNA accounted for 70%-80% of DNA, and the $OD_{260}/OD_{280}$ ratio ranged from 1.8-2.0. The concentration was not less than 0.5 μg/μl. Immediately after transplantation, 75 μg of empty vector or DNA vaccine vector was injected into mice quadriceps, and electrical stimulation was applied at the injection site. The pulse parameters were as follows: voltage, 200 V/cm; wave width, 10 ms; the number of pulses, 6; frequency, 1 Hz. For control drugs, the "gold standard" regimen CsA+MTX that was commonly used in clinical practice was used. CsA was administered via intraperitoneal injection once a day at a dose of 1.5 mg/kg·d, whereas MTX was administered via intraperitoneal injection on days 1, 3, 6, and 11 at a dose of 0.4 mg/kg·d.

1.5 Detection of Serum Cytokines in aGVHD Mice by Luminex Liquid Chip

On days 7, 14, and 21 after transplantation, blood was drawn from the infraorbital venous plexus of the mice. After the serum was separated with a centrifuge, the following procedures were performed. Each sample was examined in replicate.

1) Preparation before the experiment included the following:

Twenty milliliters of wash buffer concentrate was diluted to 500 ml of wash buffer;

The sample was diluted 4-fold: 37.5 μl of RD6-40+12.5 μl of sample;

Dilution of standard samples: the standard sample was diluted with 0.9 ml of RD6-40 into a standard cocktail, which was then progressively diluted into varying concentrations;

Dilution of microsphere: 50 μl of microsphere concentrate→5 ml of microsphere diluent;

Dilution of biotin-antibody: 50 μl of biotin-antibody concentrate→5 ml of biotin-antibody diluent;

Dilution of streptavidin-PE: 55 μl of streptavidin-PE concentrate→5.5 ml wash buffer.

2) All reagents, standards, and samples were prepared at room temperature.

3) One hundred microliters of wash buffer was used to pre-wet the membrane on the microplate and remove the liquid with vacuum washer.

4) The diluted microspheres were re-suspended by gently shaking the shaker, and then 50 μl of microspheres was added to each well.

5) After 50 μl of sample or standard sample was added to each well, the wells were sealed, followed by incubation at room temperature in the dark (covered with aluminum foil) for 3 h.

6) The liquid was removed with a vacuum washer, and the plate was washed 3 times with 100 μl of wash buffer.

7) After 50 μl of a diluted mixture of biotin-antibodies was added, the wells were sealed with a membrane, followed by incubation while shaking at 500±50 rpm at room temperature in the dark (covered with aluminum foil) for 1 h.

8) The plate was washed 3 times, as described in 6).

9) After 50 μl of diluted streptavidin-PE was added to each well, the wells were sealed with membrane, followed by incubation while shaking at 500±50 rpm at room temperature in the dark (covered with aluminum foil) for 0.5 h.

10) The plate was washed 3 times, as described in 6).

11) After 100 μl of wash buffer was added to each well to re-suspend the cells, the plate was shaken at 500±50 rpm at room temperature for 2 min.

12) The analysis was conducted with a Luminex™ 100 instrument within 90 min.

1.6 Detection of Serum Cytokines in aGVHD Mice by ELISA Kit

Because lacking the matching mouse TGFβ Luminex kit and ELISA kit, we used the human TGF-β ELISA kit as a substitute reagent in view of the fact that there is high homology between human TGF-β and mouse TGF-β. It is difficult to determine the serum IL-2 concentration. But when a T cell is activated, IL-2 binds to its receptors (with α, β, and γ subunits), and the α subunit falls off of the cell surface and can be detected in the serum, called soluble IL-2 receptor (sIL-2R). Thus, an ELISA kit can be used to re-detect sIL-2R in mice.

The methods for detecting serum sIL-2R in mice and human TGFβ were as follows:

1) The required plate was taken out of the sealed bag after pre-equilibration to room temperature.

2) One well was left blank, and the sample (1:1 dilution) and different concentrations of standard samples (100 μl/well) were added to the other wells. The wells were then sealed with a plate cover and incubated in an incubator at 37° C. for 90 min.

3) The plate was washed 4 times. Except for the blank well, biotin-antibody working solution (100 μl/well) was added to each well. The wells were then sealed with a plate cover and incubated in an incubator at 37° C. for 60 min.

4) The plate was washed 4 times. Except for the blank well, enzyme-conjugating working solution (100 μl/well) was added. The wells were then sealed with a plate cover and incubated in an incubator at 37° C. for 30 min.

5) The plate was washed 4 times. The chromogenic agent (100 μl/well) was added, and then the plate was incubated in an incubator at 37° C. in the dark for 10-15 min.

6) The stop solution (1001/well) was added and mixed well, and $OD_{450}$ value was measured immediately (within 5 min).

Interpretation of the Results:

CurveExpert 1.3 software was used to graph the standard curve. The concentrations of the standard samples were used as the abscissa, and OD values were used as the ordinates to graph the standard curve. The concentrations of the samples can be determined on the standard curve by using their OD values. If the OD value of a sample was higher than the upper limit of the standard curve, the sample was appropriately diluted for re-measurement. The dilution fold was then multiplied while calculating the concentration of the sample.

1.7 Analysis of Peripheral T-Cell Subpopulations in aGVHD Mice

At week 2 after transplantation, peripheral blood was drawn and treated with heparin sodium. Then, FITC-anti-mouse CD3, PE-anti-mouse CD28, PE-Cy5-anti-mouse CD8, PE-Cy5-anti-mouse CD4, PE-anti-mouse CD4, and PE-anti-mouse CD25 monoclonal antibodies were added. Flow cytometric analysis was conducted to detect changes in the $CD4^+/CD8^+$ and $CD3^+CD8^+C28^-$ inhibitory T-cell subpopulations (Ts cells) and the $CD4^+CD25^+$ regulatory T-cell subpopulation (Treg cells). The methods were as follows:

1) After 1 μg of corresponding fluorescent-labeled antibodies was added to 100 μl of anticoagulant blood, the sample was incubated at room temperature in the dark for 30 min.

2) Two milliliters of Pharmlyse™ erythrocyte lysis buffer was added, followed by incubation at room temperature in the dark for 15 min.

3) The sample was centrifuged at 1500 rpm for 6 min, re-suspended with PBS after the supernatant was discarded, and then centrifuged at 1500 rpm for 5 min again.

4) The supernatant was discarded, and 0.5 ml of 2% paraformaldehyde/PBS was added for detection.

1.8 Statistical Analysis

The data were expressed as x̄+s, and SPSS 13.0 software was used for statistical analysis. ANOVA and Dunnett's t-test were used for comparison among groups when there was homogeneity of variance. $P<0.05$ is considered statistically significant. Non-parametric analysis was used when there was heterogeneity of variance.

2. Results 2.1 The Changes of Serum Cytokines in aGVHD Mice after Treatment with B7-1-PE40KDEL DNA Vaccine On days 7, 14, and 21 after transplantation, Luminex liquid chip and the ELISA method were used to detect the changes of serum cytokines in the mice of all experimental groups. The results are presented in Table 1. The results revealed that among Th1 cytokines, the levels of IFNγ, IL-2, and TNFα were significantly higher in aGVHD mice than in the normal control group ($P<0.01$), especially during the time period from the beginning stage of the disease's onset to day 7 after transplantation. By day 14 after transplantation, the IFNγ level gradually declined, and by day 21, IFNγ had returned to a near-normal level. In contrast, the levels of IL-2 and TNFα, two of the Th1 cytokines, were maintained at levels far higher than normal. There was no statistical difference in the changes of IL-4 (Th2 cytokine) and TGF-3 (Th3 cytokine) levels between the experimental groups and the normal control group. Surprisingly, on days 7 and 14, the IL-10 (Th2 cytokine) level was significantly higher in aGVHD mice than in the normal control group. Due to the sensitivity of the available detection methods, it was difficult to detect IL-12.

As shown in Table 5, during the 7 days after transplantation, the decline of serum Th1 cytokines such as IFNγ was the most significant ($P<0.01$) in the mice in B7-1-PE40KDEL DNA vaccine group, B7-2-PE40KDEL DNA vaccine group and B7-1-PE40KDEL+B7-2-PE40KDEL DNA vaccine group. The IFNγ level was still high on day 7 in CsA+MTX group, and the difference was statistically significant when compared with that in the aGVHD group ($P<0.01$). However, on days 14 and 21, similar to the B7-1-PE40KDEL DNA vaccine group, IFNγ level returned to normal in CsA+MTX group. In addition, IL-2 level was effectively reduced in both B7-1-PE40KDEL DNA vaccine group and CsA+MTX group, and the difference was statistically significant when compared with that in the aGVHD control group ($P<0.05$). In contrast, the effect on the Th1 cytokine TNF-α was not significant in either B7-1-PE40KDEL DNA vaccine group or CsA+MTX group.

As shown in Table 5, for Th2 cytokines such as IL-4 and IL-10 and Th3 cytokine TGF-β, which are involved in the suppression of inflammation, there was no statistical difference in the effect on Th2 cytokine IL-4 between B7-1-PE40KDEL DNA vaccine group and CsA+MTX group. The levels of Th2 cytokine IL-10 were effectively increased in both B7-1-PE40KDEL DNA vaccine group and CsA+MTX group, and the difference was statistically significant when compared with the level in the aGVHD control group. For the Th3 cytokine TGF-β, only B7-1-PE40KDEL DNA vaccine effectively increased its level, and B7-2-PE40KDEL DNA vaccine group had no significant effect. In contrast, CsA+MTX group slightly decreased the expression level of Th3 cytokine TGF-β.

TABLE 5

The effect of B7-1-PE40KDEL DNA vaccine on Th1, Th2, and Th3 cytokines in the peripheral blood of aGVHD mice

| Group | Th1, Th2, and Th3 cytokines (pg/ml) | | | | | |
| --- | --- | --- | --- | --- | --- | --- |
| | INF-γ | TNF-α | IL-2 | IL-4 | IL-10 | TGF-β |
| Normal group + day 7 | 0 | 0.52 ± 0.27 | 11.17 ± 3.47 | 284.50 ± 22.18 | 4.70 ± 0.78 | 1072.55 ± 147.85 |
| +day 14 | 0 | 0.52 ± 0.27 | 11.17 ± 3.47 | 284.50 ± 22.18 | 4.70 ± 0.78 | 1072.55 ± 147.85 |
| +day 21 | 0 | 0.52 ± 0.27 | 11.17 ± 3.47 | 284.50 ± 22.18 | 4.70 ± 0.78 | 1072.55 ± 147.85 |
| NS group + day 7 | 1465.03 ± 316.77 | 19.97 ± 3.69 | 20.54 ± 1.58 | 277.94 ± 22.14 | 8.76 ± 0.53 | 1239.27 ± 450.30 |
| +day 14 | 122.37 ± 49.38 | 11.24 ± 0.73 | 23.44 ± 2.52 | 271.03 ± 22.62 | 9.99 ± 2.15 | 1036.73 ± 268.11 |

TABLE 5-continued

The effect of B7-1-PE40KDEL DNA vaccine on Th1, Th2, and Th3 cytokines in the peripheral blood of aGVHD mice

| Group | Th1, Th2, and Th3 cytokines (pg/ml) | | | | | |
|---|---|---|---|---|---|---|
| | INF-γ | TNF-α | IL-2 | IL-4 | IL-10 | TGF-β |
| +day 21 | 12.29 ± 8.69 | 9.64 ± 3.72 | 23.43 ± 0.89 | 268.76 ± 29.97 | 6.88 ± 1.40 | 1378.67 ± 541.84 |
| Vector group + day 7 | 1053.63 ± 109.48 | 15.47 ± 1.25 | 29.47 ± 1.58 | 272.80 ± 17.47 | 9.29 ± 1.63 | 1080.59 ± 275.75 |
| +day 14 | 73.94 ± 24.60 | 13.30 ± 1.45 | 21.65 ± 1.26 | 225.88 ± 27.93 | 10.72 ± 0.88 | 1146.16 ± 231.18 |
| +day 21 | 13.69 ± 6.26 | 13.15 ± 2.38 | 19.65 ± 1.58 | 238.48 ± 29.56 | 6.36 ± 1.51 | 1071.19 ± 88.58 |
| CsA + MTX + day 7 | 1874.66 ± 102.67 | 14.58 ± 0.36 | 17.83 ± 2.25 | 297.65 ± 19.15 | 11.57 ± 2.29 | 908.40 ± 141.63 |
| +day 14 | 0 | 10.43 ± 3.33 | 19.39 ± 4.45 | 232.96 ± 15.66 | 7.47 ± 1.41 | 873.54 ± 136.44 |
| +day 21 | 0 | 21.81 ± 6.29 | 17.41 ± 3.46 | 286.30 ± 33.10 | 10.32 ± 2.62 | 972.62 ± 186.71 |
| B7-1-PE40KDEL + day 7 | 533.10 ± 122.13 | 19.61 ± 1.06 | 18.31 ± 1.58 | 304.99 ± 26.43 | 12.40 ± 1.88 | 1045.65 ± 124.69 |
| +day 14 | 0 | 15.58 ± 3.22 | 20.09 ± 0.95 | 268.46 ± 3.60 | 12.29 ± 2.51 | 1601.20 ± 484.05 |
| +day 21 | 0 | 10.43 ± 3.33 | 23.44 ± 1.90 | 255.04 ± 10.23 | 7.47 ± 0.28 | 1526.97 ± 402.29 |
| B7-2-PE40KDEL + day 7 | 602.20 ± 101.64 | 20.08 ± 5.27 | 14.04 ± 3.12 | 272.86 ± 26.22 | 13.03 ± 1.68 | 1036.53 ± 76.14 |
| +day 14 | 14.63 ± 7.52 | 17.86 ± 2.13 | 17.19 ± 1.90 | 273.75 ± 20.84 | 12.08 ± 1.33 | 1205.81 ± 122.57 |
| +day 21 | 0 | 15.72 ± 1.97 | 11.39 ± 2.52 | 255.88 ± 18.82 | 12.50 ± 1.33 | 1363.53 ± 366.11 |
| B7-1 + B7-2-PE40KDEL + day 7 | 419.59 ± 137.29 | 16.73 ± 0.18 | 15.85 ± 8.20 | 261.58 ± 18.46 | 11.97 ± 0.63 | 1322.33 ± 245.55 |
| +day 14 | 0 | 12.14 ± 1.28 | 3.18 ± 5.68 | 257.22 ± 10.24 | 10.75 ± 3.21 | 1256.07 ± 368.46 |
| +day 21 | 0 | 17.35 ± 12.13 | 21.65 ± 1.26 | 247.09 ± 15.32 | 9.49 ± 0.29 | 847.32 ± 155.79 |

2.2 The Changes of Peripheral T-Cell Subpopulations in aGVHD Mice after Treatment with the B7-1-PE40KDEL DNA Vaccine During week 2 after transplantation, flow cytometric analysis was conducted to detect three T-cell subpopulations (i.e., $CD4^+/CD8^+$, $CD4^+CD25^+Treg$ and $CD8^+C28^-Ts$ subpopulations). The results and representative photos are presented in FIGS. 26-31 and Table 6.

The results indicated that in the normal group, CD4/CD8 ratio was approximately 3.2, which was seriously inverted in aGVHD mice after radiation and transplantation. In aGVHD mice after radiation and transplantation compared with the normal group, $CD3^+CD8^+$T-cell proportions were significantly increased, whereas $CD3^+CD4^+$ proportions were significantly decreased. B7-1-PE40KDEL DNA vaccine and B7-2-PE40KDEL DNA vaccines, B7-1-PE40KDEL+B7-2-PE40KDEL DNA vaccine, and CsA+MTX treatment did not significantly reverse CD4/CD8 ratio (FIGS. 26-27 and Table 6).

To determine whether specific T cell subpopulations participate in immune regulation in the B7-1-PE40KDEL DNA vaccine group and CsA+MTX group, we compared the changes of $CD4^+CD25^+Treg$ proportions among $CD4^+$ lymphocytes in each group and the control group (FIGS. 28-29 and Table 5). The results revealed that $CD4^+CD25^+Treg$ proportions were significantly higher in the B7-1-PE40KDEL DNA vaccine group and B7-1-PE40KDEL+B7-1-PE40KDEL DNA vaccines group than in the empty vector group and the NS control group (P<0.01 & P<0.05). The $CD4^+CD25^+Treg$ proportions were also higher in B7-2-PE40KDEL DNA vaccine group than in the empty vector group and the NS control group (P<0.05), but the effect of B7-2-PE40KDEL DNA vaccine was weaker than that of B7-1-PE40KDEL DNA vaccine. In contrast, there was no significant difference in $CD4^+CD25^+Treg$ proportions in CsA+MTX group.

In addition, we also compared the changes in the regulation of the immune network by another regulatory T-cell (i.e., the changes in $CD8^+CD28^-Ts$ proportions among all groups). The results are shown in FIGS. 30-31 and Table 6. It can be seen that $CD8^+CD28^-Ts$ proportions were higher in B7-1-PE40KDEL DNA vaccine, B7-2-PE40KDEL DNA vaccine, B7-1-PE40KDEL+B7-2-PE40KDEL DNA vaccine and CsA+MTX groups than in the empty vector group and the NS control group, and the differences were significant (P<0.01).

TABLE 6

The effect of B7-1-PE40KDEL DNA vaccine on $CD4^+CD25^+$ and $CD8^+CD28^-$T sub-groups and CD4/CD8 ratios in the peripheral blood of aGVHD mice

| Group | | % $CD4^+CD25^+$T | % $CD8^+CD28^-$T | CD4/CD8 Ratio |
|---|---|---|---|---|
| Normal group | + day 7 | 1.53 ± 0.60 | 14.46 ± 1.50 | 3.25 ± 0.84 |
| | + day 14 | 1.53 ± 0.60 | 14.46 ± 1.50 | 3.25 ± 0.84 |
| | + day 21 | 1.53 ± 0.60 | 14.46 ± 1.50 | 3.25 ± 0.84 |
| NS group | + day 7 | 2.04 ± 1.05 | 0.89 ± 0.94 | 0.31 ± 0.02 |
| | + day 14 | 1.25 ± 0.34 | 9.18 ± 6.34 | 0.23 ± 0.01 |
| | + day 21 | 1.32 ± 0.40 | 7.25 ± 2.18 | 0.42 ± 0.09 |
| Vector group | + day 7 | 1.38 ± 0.59 | 0.69 ± 0.12 | 0.31 ± 0.01 |
| | + day 14 | 1.31 ± 0.44 | 14.64 ± 1.25 | 0.21 ± 0.04 |
| | + day 21 | 1.32 ± 0.43 | 5.66 ± 2.53 | 0.42 ± 0.07 |
| CsA + MTX | + day 7 | 1.55 ± 1.06 | 1.71 ± 0.66 | 0.27 ± 0.04 |
| | + day 14 | 1.27 ± 0.27 | 14.39 ± 1.71 | 0.24 ± 0.03 |
| | + day 21 | 1.38 ± 1.05 | 6.33 ± 2.93 | 0.45 ± 0.04 |
| B7-1-PE40KDEL | + day 7 | 1.73 ± 0.72 | 2.01 ± 0.24 | 0.34 ± 0.04 |
| | + day 14 | 2.22 ± 0.50 | 18.76 ± 6.21 | 0.19 ± 0.02 |
| | + day 21 | 4.88 ± 4.18 | 5.71 ± 1.01 | 0.44 ± 0.11 |
| B7-2-PE40KDEL | + day 7 | 1.11 ± 0.51 | 2.55 ± 0.64 | 0.27 ± 0.03 |
| | + day 14 | 1.93 ± 1.21 | 22.67 ± 6.74 | 0.20 ± 0.03 |
| | + day 21 | 1.39 ± 0.36 | 9.54 ± 2.94 | 0.39 ± 0.02 |

TABLE 6-continued

The effect of B7-1-PE40KDEL DNA vaccine on CD4+CD25+ and CD8+CD28−T sub-groups and CD4/CD8 ratios in the peripheral blood of aGVHD mice

| Group | | % CD4+CD25+T | % CD8+CD28−T | CD4/CD8 Ratio |
|---|---|---|---|---|
| B7-1 + B7-2-PE40KDEL | + day 7 | 2.59 ± 2.04 | 2.51 ± 0.34 | 0.27 ± 0.01 |
| | + day 14 | 1.94 ± 0.14 | 20.20 ± 5.44 | 0.20 ± 0.01 |
| | + day 21 | 1.96 ± 0.11 | 6.41 ± 3.00 | 0.29 ± 0.05 |

The invention includes the following non-limited embodiments:

1. A gene which encodes an exotoxin fusion protein B7-1-PE40KDEL, wherein the nucleotide sequence of said gene is
   (1) A sequence shown in SEQ ID NO: 1 or SEQ ID NO: 2,
   (2) A sequence which encodes the same protein encoded by the sequences shown in SEQ ID NO:1 or SEQ ID NO:2, and the nucleotide sequences differs from the sequences shown in SEQ ID NO:1 or SEQ ID NO:2 due to the codon degeneracy,
   (3) A sequence which hybridizes with the sequences shown in SEQ ID NO:1 or SEQ ID NO:2 under strict hybridizing conditions, and the protein encoded by said sequence having the same or similar function as the protein encoded by the sequence shown in SEQ ID NO:1 or SEQ ID NO:2, or
   (4) A sequence having more than 75% identity with the sequence shown in SEQ ID NO:1 or SEQ ID NO:2, preferably, more than 85%.
2. An exotoxin fusion protein which is encoded by the gene according to embodiment 1.
3. A recombinant expression vector which is operationally linked to the gene according to embodiment 1, and said expression vector is selected from eukaryotic expression vectors or prokaryotic expression vectors, preferably, said gene is operationally linked to anyone of the expression vectors selected from pcDNA3.1/Zeo(+), pWLNEO, pSV2CAT, pOG44, pXT1, pSG, pSVK3, pBPV, pMSG, pSVL, and adenovirus.
4. The recombinant expression vector according to embodiment 3, which consists of the gene of embodiment 1 and the pcDNA3.1/Zeo(+) vector.
5. A composition which contains the gene according to embodiment 1, the exotoxin fusion protein according to embodiment 2, or the recombinant expression vector according to embodiment 3 or 4.
6. A vaccine, which contains the gene according to embodiment 1, the exotoxin fusion protein according to embodiment 2, or the recombinant expression vector according to embodiment 3 or 4, and the pharmaceutical acceptable adjuvant.
7. A DNA vaccine which comprises the recombinant expression vector according to embodiment 3 or 4, and the pharmaceutically acceptable immune adjuvants.
8. A formulation of the composition according to embodiment 5, the vaccine according to embodiment 6, or the DNA vaccine according to embodiment 7, which be prepared in the form are suitable for the administration via intravenous injection, intra-arterial injection, intramuscular injection, subcutaneous injection, organ injection, intra-pleural injections, and intraperitoneal injection.
9. The composition according to embodiment 5, the vaccine according to embodiment 6, or the DNA vaccine according to embodiment 7, which be formulated in the form of an aqueous solution or a reconstituted freeze-dried powder, can be use in the way of injection or administration via the mucosa.
10. A method for treating or preventing allogeneic tissue and/or organ transplant rejections, comprise to administrate the composition according to embodiment 5, the vaccine according to embodiment 6, or the DNA vaccine according to embodiment 7 in an effective amount to the subject in need thereof.
11. A use of the composition according to embodiment 5, the vaccine according to embodiment 6, or the DNA vaccine according to embodiment 7 in the preparation of a medicine for treating or preventing allogeneic tissue and/or organ transplant rejections.

The embodiments of the invention have been described in detail and will be understood by a person skilled in the art. The details can be modified and substituted according to the published literature. These changes are within the scope of protection of this invention. The full scope of the invention is provided by the appended claims and any equivalents thereof.

The invention claimed is:

1. A non-naturally occurring DNA construct encoding exotoxin fusion protein B7-1-PE40KDEL
   that comprises a polynucleotide sequence having at least 95% identity to the entire length of SEQ ID NO: 1 or at least 95% identity to the entire length SEQ ID NO: 2; or a polynucleotide sequence that encodes the same protein as the polynucleotide sequence of SEQ ID NO: 1 or SEQ ID NO: 2, and
   that encodes an exotoxin fusion protein that when administered to a mammal immunosuppresses T cells.

2. An exotoxin fusion protein encoded by the DNA construct of claim 1.

3. A recombinant expression vector which is operably-linked to the DNA construct of claim 1.

4. The recombinant expression vector of claim 3, which when transfected into a eukaryotic cell is transcribed and translated into a polypeptide that is secreted extracellularly.

5. A composition comprising the DNA construct of claim 1.

6. A composition comprising the exotoxin fusion protein of claim 2 and a pharmaceutical acceptable adjuvant.

7. A composition comprising the recombinant expression vector of claim 3, and a pharmaceutically acceptable immune adjuvant.

8. A formulation of the composition of claim 5, which is suitable for administration via intravenous injection, intra-arterial injection, intramuscular injection, subcutaneous injection, organ injection, intra-pleural injection, or intraperitoneal injection.

9. The composition of claim 5, in a form of an aqueous solution or a reconstituted freeze-dried powder, suitable for injection or administration via a mucosa.

10. A method for treating or inhibiting rejection of an allogeneic tissue or an organ transplant, the method comprising administering the composition of claim 5 in an effective amount to a subject in need thereof.

11. The DNA construct of claim 1 comprising the sequence of SEQ ID NO: 1.

12. The DNA construct of claim 1, comprising the sequence of SEQ ID NO: 2.

13. The DNA construct of claim 1, comprising a nucleotide sequence that encodes the same protein as that encoded by the polynucleotide sequence of SEQ ID NO: 1 or SEQ ID NO: 2, wherein the nucleotide sequence differs from SEQ ID NO: 1 or SEQ ID NO: 2 due to codon degeneracy.

14. An expression vector comprising the DNA construct of claim 1 and plasmid pcDNA3.1/Zeo(+) that when transfected into a eukaryotic cell is transcribed and translated into a polypeptide that is secreted extracellularly.

15. A composition comprising the expression vector of claim 14 and a pharmaceutically acceptable adjuvant.

16. Expression vector pcDNA3.1/Zeo(+)-B7-1-PE40KDEL.

17. A composition comprising the expression vector of claim 16 and a pharmaceutically acceptable adjuvant.

18. An isolated gene encoding exotoxin fusion protein B7-1-PE40KDEL that comprises:
(1) the nucleotide sequence of SEQ ID NO: 1 or SEQ ID NO: 2, or
(2) a nucleotide sequence encoding the same exotoxin fusion protein encoded by the nucleotide sequence of SEQ ID NO:1 or SEQ ID NO:2, wherein the nucleotide sequence differs from SEQ ID NO:1 or SEQ ID NO:2 due to codon degeneracy.

19. A method for treating graft-vs-host disease, host-vs-graft disease or another condition mediated by activation of T cells comprising administering to a subject in need thereof the non-naturally-occurring DNA construct of claim 1.

\* \* \* \* \*